US012440623B2

(12) United States Patent
Halvorsen, Jr. et al.

(10) Patent No.: US 12,440,623 B2
(45) Date of Patent: Oct. 14, 2025

(54) ASSEMBLABLE COMPACT SYRINGE WITH SIDE MOUNTED PLUNGER ROD

(71) Applicant: Pacto Medical Inc., Homestead, PA (US)

(72) Inventors: George Robert Halvorsen, Jr., San Diego, CA (US); Ian Speers, Washington, DC (US); Ryan Stinebaugh, Homestead, PA (US)

(73) Assignee: Pacto Medical Inc., Homestead, PA (US)

( * ) Notice: Subject to any disclaimer, the term of this patent is extended or adjusted under 35 U.S.C. 154(b) by 0 days.

(21) Appl. No.: 18/591,453

(22) Filed: Feb. 29, 2024

(65) Prior Publication Data

US 2024/0293623 A1 Sep. 5, 2024

Related U.S. Application Data

(60) Provisional application No. 63/487,680, filed on Mar. 1, 2023.

(51) Int. Cl.
*A61M 5/315* (2006.01)
*A61M 5/31* (2006.01)

(52) U.S. Cl.
CPC . *A61M 5/31515* (2013.01); *A61M 2005/3142* (2013.01); *A61M 2207/10* (2013.01)

(58) Field of Classification Search
CPC .......... A61M 5/31515; A61M 5/31511; A61M 5/31565; A61M 5/3135; A61M 5/28;
(Continued)

(56) References Cited

U.S. PATENT DOCUMENTS 4,011,868 A * 3/1977 Friend ................. A61M 5/5086
604/218
4,581,023 A 4/1986 Kuntz
(Continued)

FOREIGN PATENT DOCUMENTS

EP 2793983 A1 6/2013
WO 1997029798 A1 8/1997
(Continued)

OTHER PUBLICATIONS

International Search Report and Written Opinion issued for PCT International Application No. PCT/US2024/017818 dated Jun. 24, 2024, 11 pages.

*Primary Examiner* — Michael J Tsai
*Assistant Examiner* — Justin L Zamory
(74) *Attorney, Agent, or Firm* — Duane Morris LLP

(57) ABSTRACT

A syringe, a kit, methods of making and methods of using the same are provided. The syringe includes a syringe body defining an interior volume. The syringe body defines a first opening at a distal end for dispensing and a second opening at a proximal end. The syringe further includes a stopper disposed inside the barrel, optionally a stopper insert coupled with the stopper, and a plunger rod disposed outside the syringe body. The plunger rod has a first end, a second end, and a middle section. The middle section is disposed along the barrel wall. The first end of the plunger rod is configured to be coupled with the stopper or the stopper insert, and the second end is reversibly attached to the distal end or the proximal end of the syringe body. The plunger rod can be detached and assembled with the stopper or the stopper insert so as to drive the stopper for injection.

18 Claims, 24 Drawing Sheets

(58) Field of Classification Search
CPC ........... A61M 2005/31518; A61M 2005/3121; A61M 2005/3194; A61M 2005/3118; A61M 2005/3142
See application file for complete search history.

(56) References Cited

U.S. PATENT DOCUMENTS

| | | | | |
|---|---|---|---|---|
| 5,067,947 | A | 11/1991 | Volk et al. | |
| D412,206 | S | 7/1999 | Basile et al. | |
| 7,569,036 | B2 * | 8/2009 | Domkowski | A61M 5/50 604/232 |
| 8,043,267 | B2 | 10/2011 | Nanba et al. | |
| 10,960,139 | B2 | 3/2021 | Schiff et al. | |
| 11,103,639 | B1 | 8/2021 | Chen et al. | |
| 11,744,950 | B2 | 9/2023 | Perez-Pacheco et al. | |
| 11,801,349 | B2 | 10/2023 | Murray et al. | |
| 2006/0151545 | A1 * | 7/2006 | Imhof | A61M 5/14566 222/390 |
| 2008/0082055 | A1 | 4/2008 | Lloyd et al. | |
| 2008/0103455 | A1 * | 5/2008 | Domkowski | A61M 5/24 604/232 |
| 2011/0046603 | A1 * | 2/2011 | Felsovalyi | A61M 5/31511 604/218 |
| 2013/0082057 | A1 | 4/2013 | Schiff et al. | |
| 2013/0085455 | A1 * | 4/2013 | Manke | A61M 5/31511 604/227 |
| 2014/0100546 | A1 | 4/2014 | Lum et al. | |
| 2021/0268197 | A1 | 9/2021 | Waller et al. | |
| 2021/0283335 | A1 | 9/2021 | Manke et al. | |

FOREIGN PATENT DOCUMENTS

| | | | |
|---|---|---|---|
| WO | 2013048874 | A1 | 4/2013 |
| WO | 2014072994 | A2 | 5/2014 |
| WO | 2017044252 | A1 | 3/2017 |
| WO | 2017046636 | A1 | 3/2017 |

* cited by examiner

ASSEMBLABLE COMPACT SYRINGE WITH SIDE MOUNTED PLUNGER ROD

PRIORITY CLAIM AND CROSS-REFERENCE

This application claims the benefit of U.S. Provisional Application No. 63/487,680, filed Mar. 1, 2023, which application is expressly incorporated by reference herein in its entirety.

FIELD OF THE INVENTION

The disclosure relates to a medical device for injection generally. More particularly, the disclosed subject matter relates to a syringe, which is prefilled or not filled; a kit comprising the syringe, methods of making the same; and methods of using the same.

BACKGROUND

A syringe is a commonly used medical device, and functions as a simple reciprocating pump. A syringe includes a plunger or piston that fits tightly within a cylindrical tube called a barrel. The plunger can be linearly pulled and pushed along the inside of the tube, allowing the syringe to take in and expel solids, liquids or gases through a discharge orifice at one end of the tube. The open end of the syringe may be fitted with a hypodermic needle, a nozzle or tubing to direct the flow of the solid, liquid or gas into and out of the barrel. Syringes are frequently used in clinical medicine to administer injections, infuse intravenous therapy into the bloodstream, apply compounds, and draw/measure liquids.

Billions of prefilled syringes are manufactured and used around the world each year for the healthcare industry alone. Existing prefilled syringes across all fields, both within and outside of the healthcare industry, are stored with their plunger rod disposed inside the barrel and fully or almost fully extended. The space consumed by the plunger rod in such designs (up to 40% of the entire packaging in the case of pre-filled syringes) wastes critical space, resources, time, and costs extra money along the entire supply chain, especially when the point of manufacture is far from the point of use. This waste and extra expense reduces access to prefilled syringes, hindering public health and emergency response efforts. It also increases the environmental footprint of the syringes, including transportation carbon and excess packaging.

SUMMARY OF THE INVENTION

The present disclosure provides a syringe, a kit comprising such a syringe, methods of making the same, and methods of using the same. Such a syringe is a compact or assemblable syringe.

In accordance with some embodiments, such a syringe comprises a syringe body, a stopper, and a plunger rod. Such a syringe may further comprise a stopper insert.

The syringe body has a distal end (or a first end), a proximal end (or a second end), and a barrel between the distal end and the proximal end. The barrel comprises a barrel wall defining an interior volume. The syringe body further defines a first opening at the distal end for dispensing and a second opening at the proximal end.

The stopper is disposed inside the barrel and is configured to seal the interior volume. The stopper insert has a distal portion and a proximal portion. The stopper insert is disposed inside the barrel and coupled with the stopper at the distal portion.

The plunger rod is disposed outside the syringe body. The plunger rod has a first end, a second end, and a middle section. The middle section is disposed along the barrel wall. In some embodiments, the first end of the plunger rod is sized and configured to be coupled with the stopper insert at the proximal portion of the stopper insert. The second end of the plunger rod is reversibly attached to the distal end or the proximal end of the syringe body. The plunger rod is configured to be detached and assembled with the stopper insert by a user so as to drive the stopper in a direction from the proximal end to the distal end of the syringe body.

In some embodiments, the stopper insert is optional and the plunger rod is sized and configured to be coupled with the stopper directly through some configurations described for the stopper insert. The stopper has the structural features described in the stopper insert. The first end of the plunger rod is sized and configured to be coupled directly with the stopper.

In some embodiments, the syringe body comprises a barrel flange on the proximal end.

In some embodiments, the plunger rod comprises a snap cylinder and defines a concave portion between the snap cylinder and the middle section. The concave portion is configured to receive a portion of the barrel flange of the syringe body.

In some embodiments, the proximal portion of the stopper insert comprises one or more cantilever arm(s). The first end of the plunger rod comprises a raised lip, which is configured to form a mechanical interlock with the cantilever arm in the stopper insert through a snap mechanism.

In some embodiments, the proximal portion of the stopper insert is flexible and has threads therein. The first end of the plunger rod comprises a barb structure having angular edged structures. The barb structure is configured to be inserted into and lock with the proximal portion of the stopper insert through the angular edged structures inside the threads.

In some embodiments, the proximal portion of the stopper insert comprises a protrusion in a middle and defines a trench around the protrusion. The first end of the plunger rod defines a hole. The first end of the plunger rod is configured to be disposed in the trench, and the protrusion is configured to be disposed inside the hole to provide a male/female interlocking structure.

In some embodiments, the first end of the plunger rod comprises a patterned tip structure. The proximal portion of the stopper insert defines a patterned depression having a shape complimentary to the patterned tip structure. The first end of the plunger rod is configured to be twistedly fitted into the proximal portion of the stopper insert.

In some embodiments, the second end of the plunger rod comprises a plunger flange configured to be reversibly attached to the distal end or the proximal end of the syringe body.

In some embodiments, the second end of the plunger rod is attached to the distal end of the syringe body.

In some embodiments, the second end of the plunger rod is attached to the proximal end of the syringe body.

In some embodiments, the plunger flange at the second end of the plunger rod defines a hole, and the second end of the plunger rod is attached to the distal end of the syringe body. The distal end of the syringe is disposed through the hole.

In some embodiments, the middle section of the plunger rod has a wall with a curved surface matching with a portion of an exterior surface of the barrel wall. The middle section of the plunger rod is proximal to or in contact with the portion of an exterior surface of the barrel wall.

In some embodiments, the syringe is a prefilled syringe, which comprises a solid, liquid, or gas therapeutic product disposed inside a portion of the interior volume between the distal end of the syringe body and the stopper. Examples of a therapeutic product include, but are not limited to, a solid, liquid, or gas pharmaceutical composition or a biological composition.

In some embodiments, the syringe further comprises a cap disposed at the distal end of the syringe body and configured to seal the first opening at the distal end for dispensing. The distal end of the syringe is configured to be attached with a needle for injection.

In another aspect, the present disclosure provides a kit comprising the syringe as described herein.

In another aspect, the present disclosure provides a kit comprising the syringe body, the stopper, the stopper insert, and the plunger rod as descried herein. The stopper insert is optional if the stopper is configured to be coupled with the plunger rod. In some embodiments, the kit includes a therapeutic product as described herein. These components can be assembled to provide a syringe such as a prefilled syringe as described herein.

In another aspect, the present disclosure provides a method of making the syringe. Such a method comprises steps of providing the syringe body, the stopper, the stopper insert, and the plunger rod; coupling the stopper insert and the stopper; inserting the stopper insert and the stopper into the barrel of the syringe body from the second opening; and attaching the plunger rod to the exterior of the syringe body. In some embodiments, the method further comprises filling a pre-determined amount of a therapeutic product into a portion of the interior volume between the distal end of the syringe body and the stopper. In some embodiments, the stopper insert is optional.

In another aspect, the present disclosure provides a method of using the syringe and the kit as described herein. The method comprises steps of detaching the plunger rod from the syringe body, and assembling the plunger rod with the stopper insert or the stopper inside the barrel. The first end of the plunger rod is coupled with a proximal end of the stopper insert or the stopper.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

DETAILED DESCRIPTION

Figure 1A:
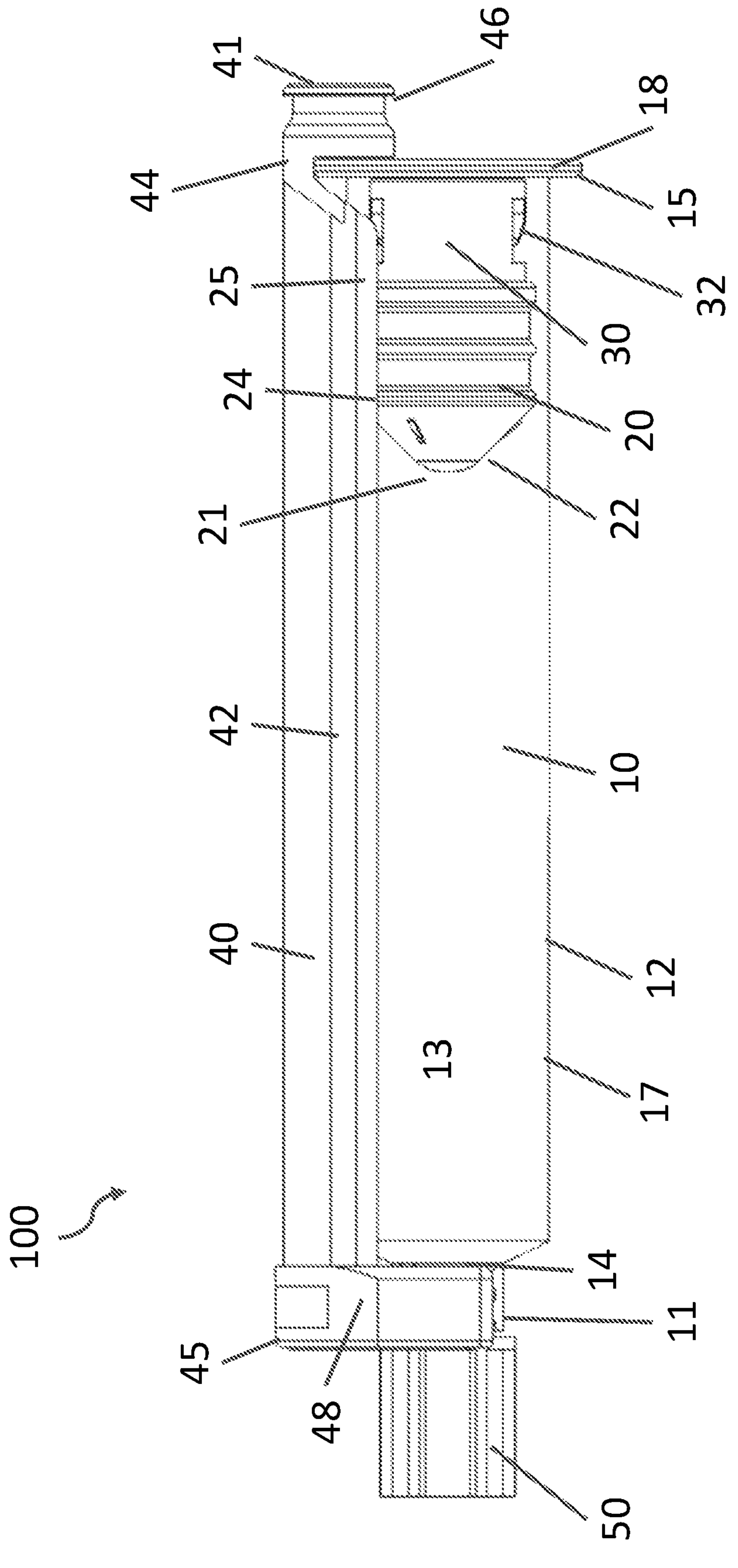
FIGS. 1A-1D are side plan views of an exemplary syringe in accordance with some embodiments.
Figure 1B:
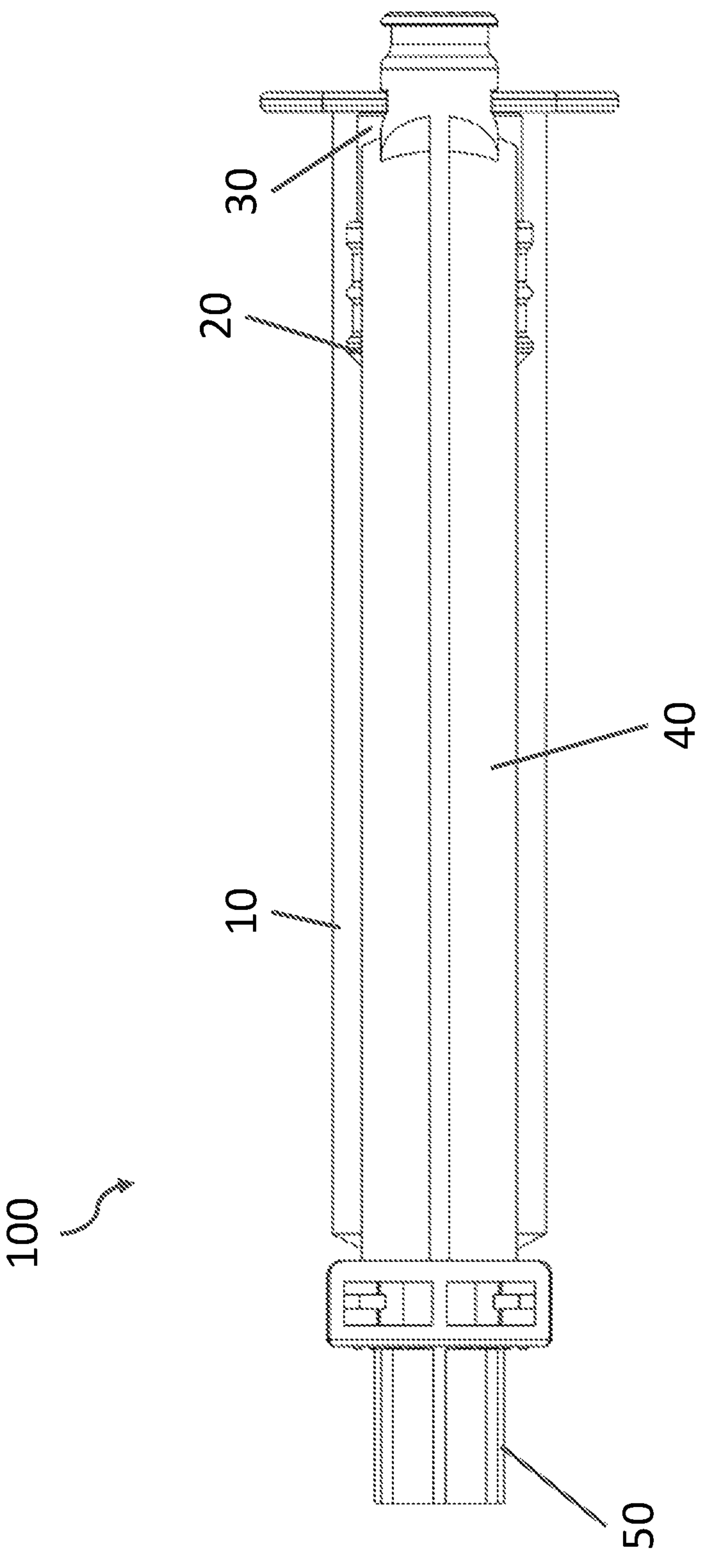
Figure 1C:
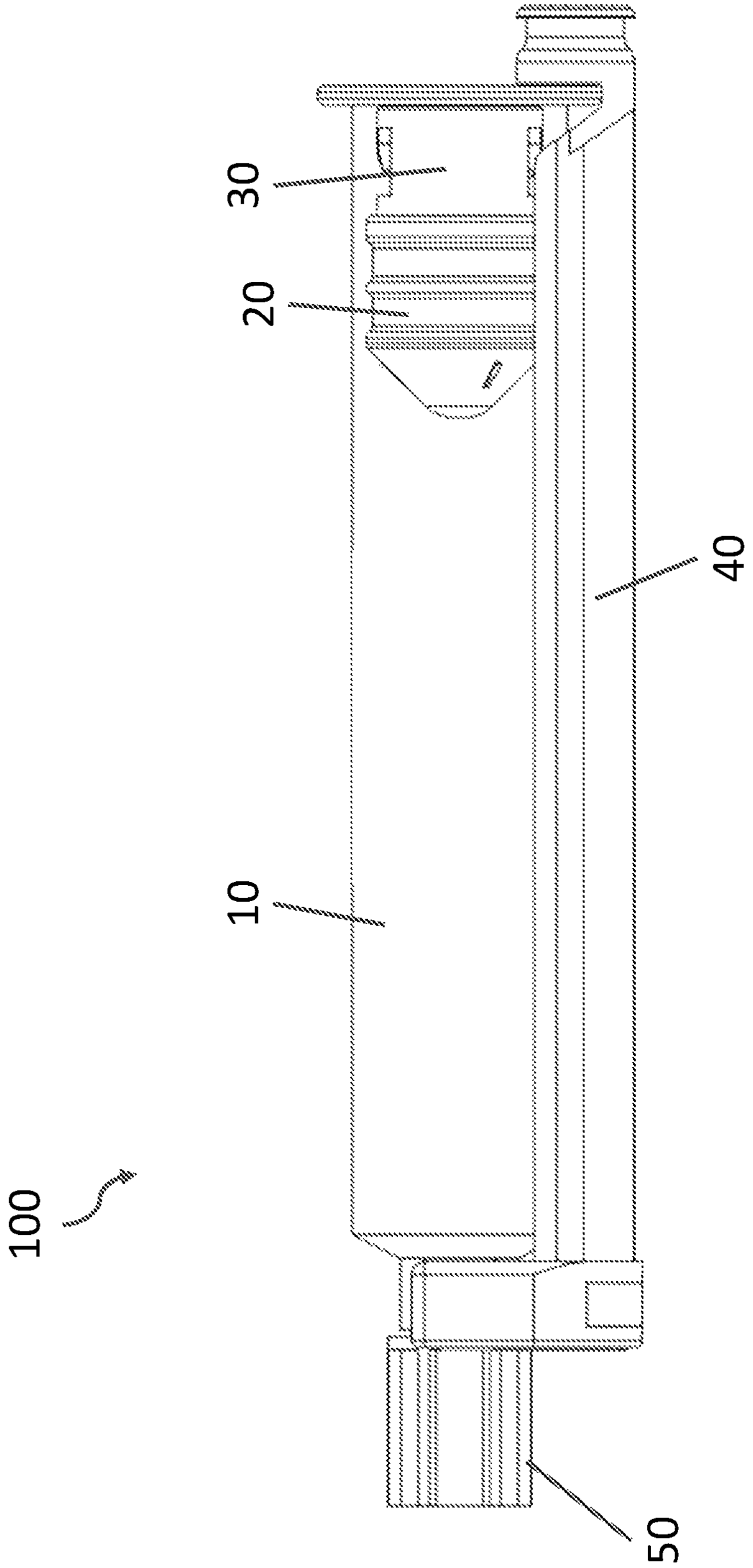
Figure 1D:
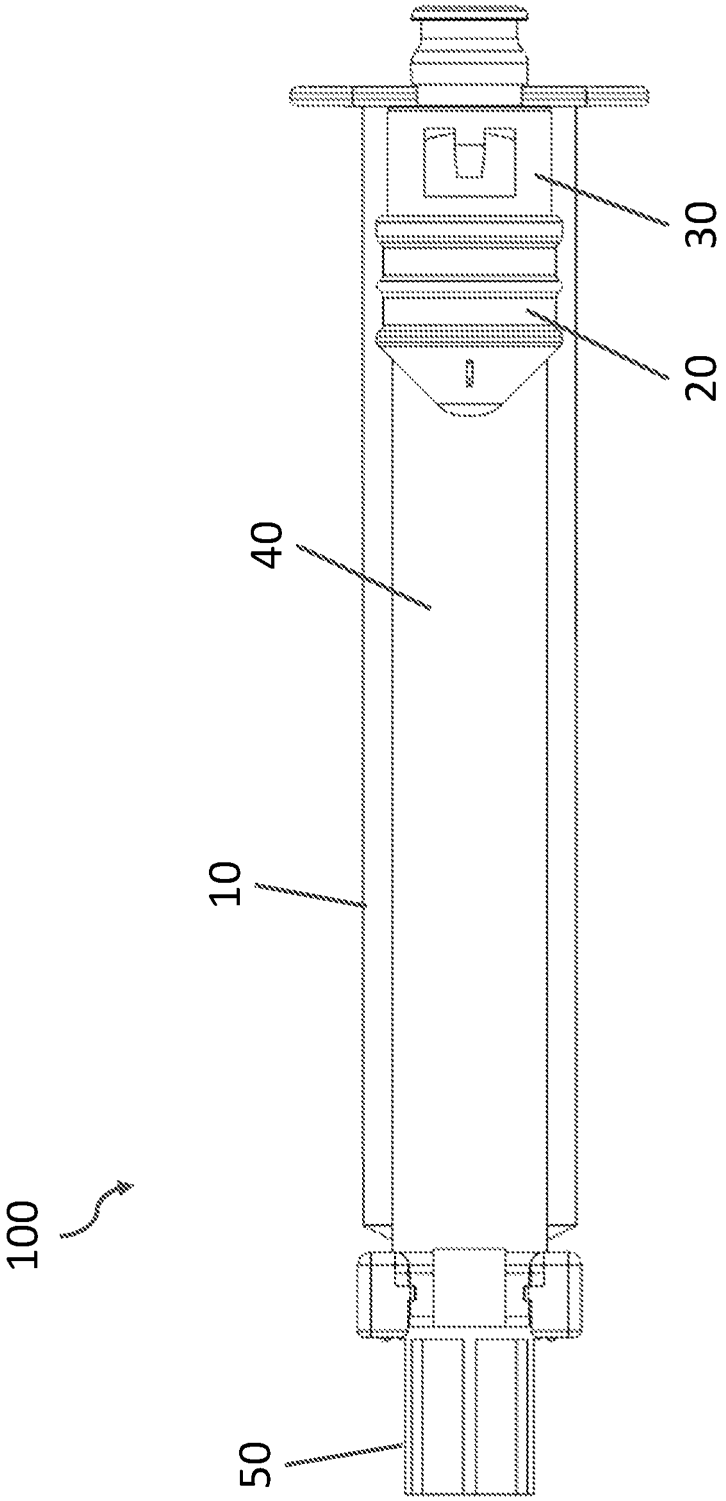

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

For purposes of the description hereinafter, it is to be understood that the embodiments described below may assume alternative variations and embodiments. It is also to be understood that the specific articles, compositions, and/or processes described herein are exemplary and should not be considered as limiting.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

For brevity, references to "a syringe" herein will be understood to encompass both a syringe without any therapeutic product and a prefilled syringe including a therapeutic product, unless expressly indicated otherwise. A therapeutic product can be in the form of a solid, a liquid, a gas, or a combination thereof.

In FIGS. 1-19, like items are indicated by like reference numerals, and for brevity, descriptions of the structure, provided above with reference to the preceding figures, are not repeated.

Figure 20:
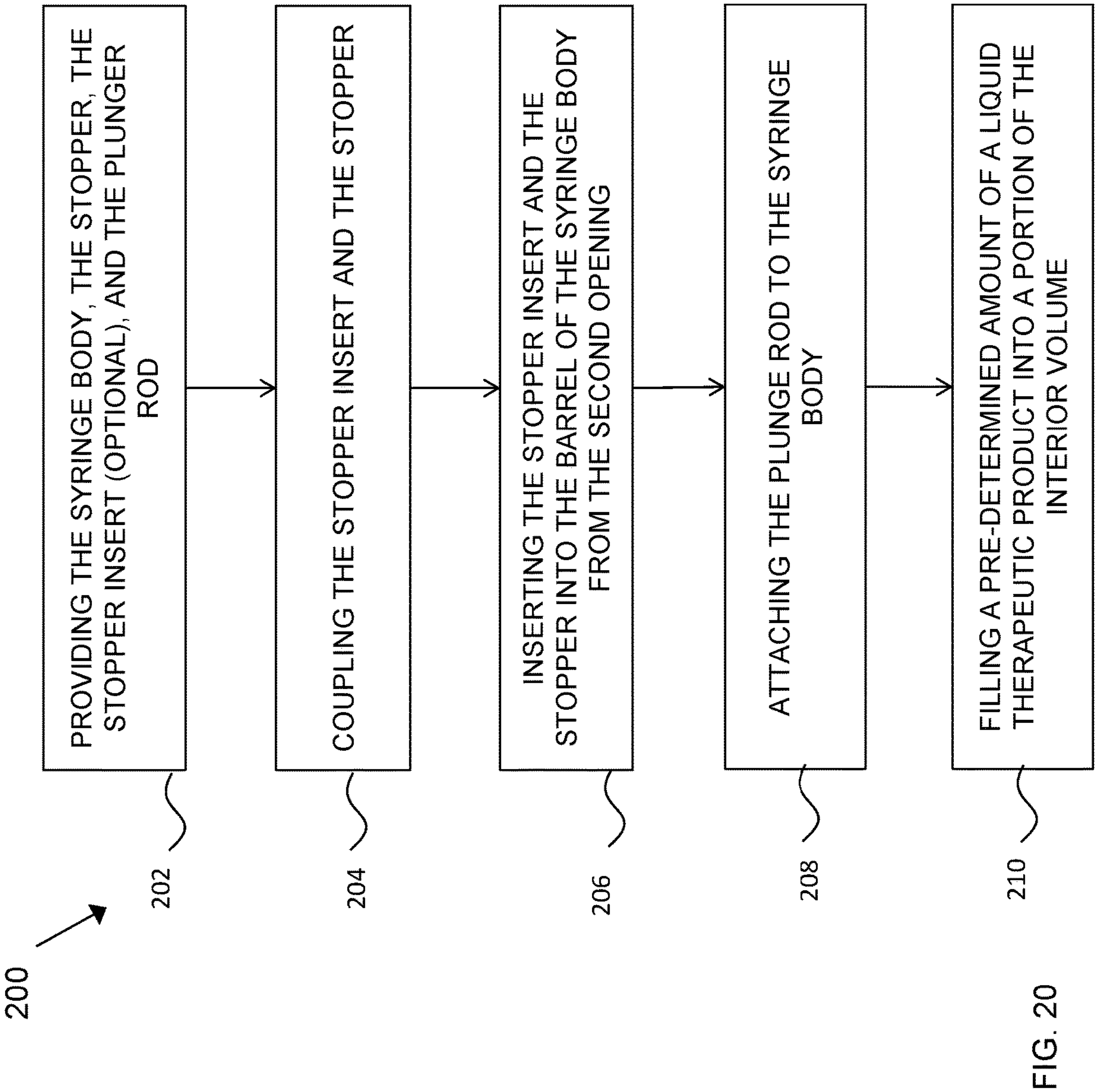
FIG. 20 is a flowchart diagram illustrating an exemplary method of making the syringe in accordance with some embodiments.
Figure 21:
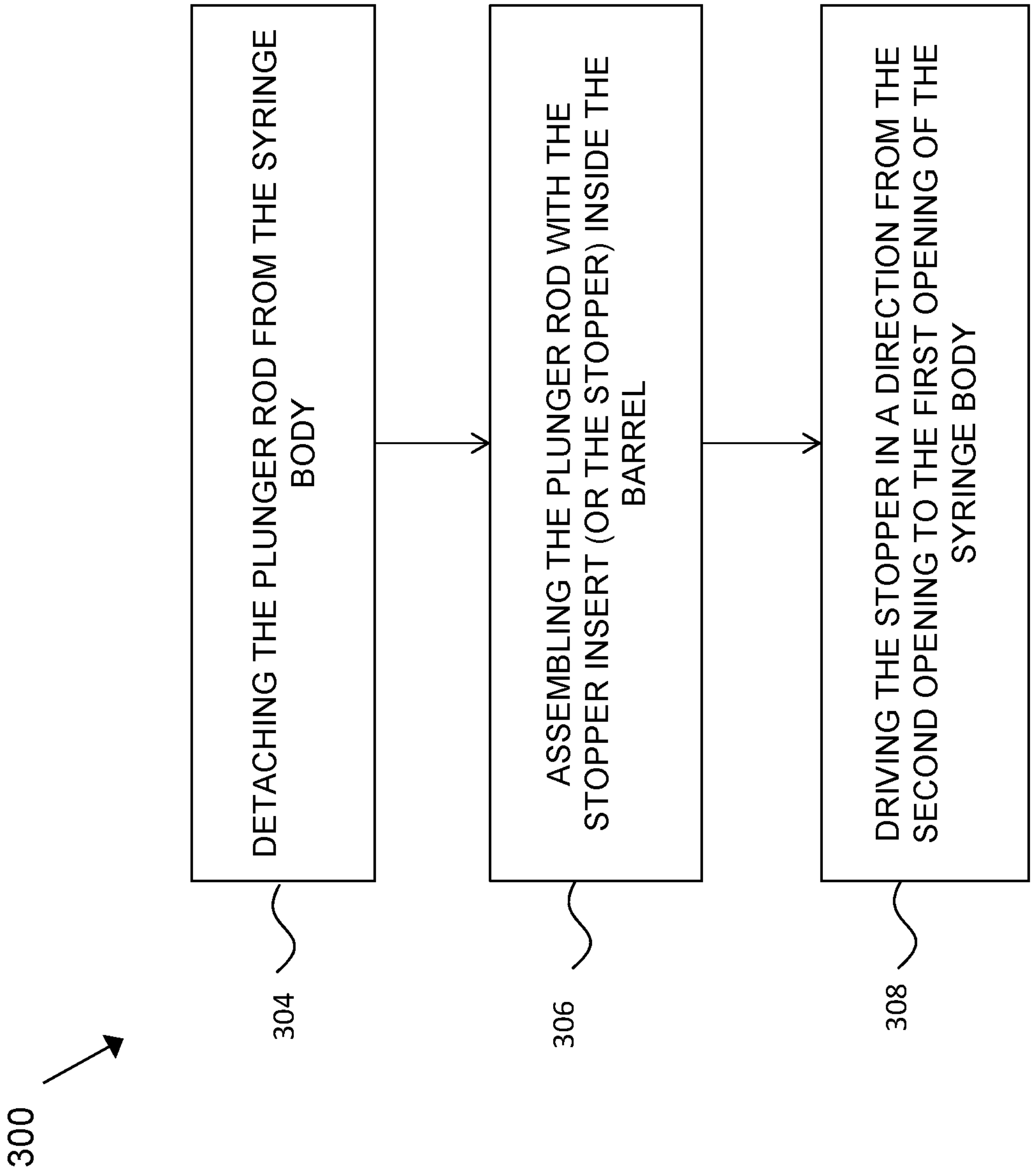
FIG. 21 is a flowchart diagram illustrating an exemplary method of using the syringe in accordance with some embodiments.

The methods described in FIGS. 20-21 are described with reference to the exemplary structure described in FIGS. 1-19.

Existing prefilled syringes are stored with their plunger rod disposed inside the barrel, and the plunger rod is fully or almost fully extended during the transportation and storage. This wastes space, resources, time, and costs extra money along the entire supply chain. The present disclosure provides a compact syringe design, which eliminates most of the extra space requirement tied to the extended plunger rod. This also lowers sterilization costs for products requiring sterilization, shipping costs, storage costs, resource requirements, supply chain bottlenecks, distribution challenges, and reduces the environmental impact of the prefilled syringes.

The present disclosure provides a syringe, a kit comprising such a syringe, methods of making the same, and methods of using the same. Such a syringe is a compact or assemblable syringe.

In some embodiments, the present disclosure provide a compact syringe, a kit comprising such a syringe, the method of making the same, and the method of using the same. These products and methods constitute novel and substantial contribution to related fields such as the medical field in terms of cost, resource, and environmental impact savings as there are currently approximately seven billion prefilled syringes manufactured around the world each year for the healthcare industry alone, for example, $8 billion dollars of annual market with an estimated CAGR (compound annual growth rate) of 10%. By reducing the cost and logistical requirements to sterilize, ship, store, distribute, and carry prefilled syringes, the cost to the end user and purchaser will also reduce, thus making prefilled syringes more affordable and accessible to those living and working in low-resource or resource-constrained settings around the world.

In the healthcare field alone, making prefilled syringe technology and options more affordable and accessible to a broad range of markets, this invention will significantly and positively contribute to global health equity. This is because, compared to drawing up solutions from vials and ampoules with empty syringes, prefilled syringes are more convenient, easier to use, more sterile, more accurate, waste less medication, and faster to use. Prefilled syringes also reduce the number of actions required with needles per injection, which leads to fewer needle stick injuries and potential injuries and illnesses. Overall, this means that prefilled syringes are more preferable and safer for both patients and healthcare providers alike.

The design herein allows for the plunger rod to stay stored and clipped securely to the side of the syringe in transit, which reduces the packaging footprint of the medical device by approximately 40% from the traditional current state. The design of an exemplary syringe described herein lowers the cost of sterilizing, shipping, storing, handling, and distributing prefilled syringes, which has a large impact throughout the supply chain in terms of cost, resource requirements, and environmental impact. To use the syringe, the plunger rod is fully removed from the side of the device and the proximal end of the plunger rod is installed into the back of the stopper using a snap-fit. The plunger rod can then be pushed or pulled, as needed and the remainder of the syringe design and usability does not differ from existing art.

The design of an exemplary syringe described herein uniquely and purposefully does not change any parts or design elements that interact directly with the solutions inside the syringe. This is important as it does not call for a full redesign or large and challenging changes to manufacturing, molding, assembly, sterilization, testing, quality assurance, or regulatory processes. This allows the inventive product design to be added into existing designs and products easier than if changing more of the structure of the prefilled syringe design, especially elements which directly interact with the solution inside the syringe.

Referring to FIGS. 1A-1D, 2-5, and 6A-6B, an exemplary syringe 100 is illustrated. In accordance with some embodiments, such a syringe 100 comprises a syringe body 10, a stopper 20, a stopper insert 30, and a plunger rod 40. FIGS. 1A-1D are side plan views of the exemplary syringe 100 in accordance with some embodiments. In FIGS. 1A, 1B, 1C, and 1D, the plunger rod 40 is shown on the top, in the front, in the bottom, and in the back of the exemplary syringe 100, respectively.

As shown in FIGS. 1A-1D and 2, the syringe body 10 has a distal end 11 (or a first end), a proximal end 15 (or a second end), and a barrel 12 between the distal end and the proximal end. The barrel 12 comprises a barrel wall 17 defining an interior volume 13. The syringe body 10 further defines a first opening 14 at the distal end 11 for dispensing and a second opening 19 at the proximal end 15.

In some embodiments, the barrel 12 has an elongated shape having a certain length. The barrel 12 may be in a cylindrical shape.

The first opening 14 for dispensing is small, while the second opening 19 is much larger for fitting the stopper 20, the stopper insert 30, and a plunger rod 40. The second opening 19 has a diameter of the same size of that of the top portion of the stopper 20.

The syringe body 10 may be transparent or semi-transparent. It can be made of a suitable material such as glass such as borosilicate glass, a polymer such as polypropylene, cyclic olefin copolymer (COC), cyclic olefin polymer (COP), and polycarbonate. Because the syringe body is transparent or semi-transparent, the stopper 20 and the stopper insert 30 disposed therein are illustrated in solid lines in FIGS. 1A-1D for illustration purposes.

Figure 2:
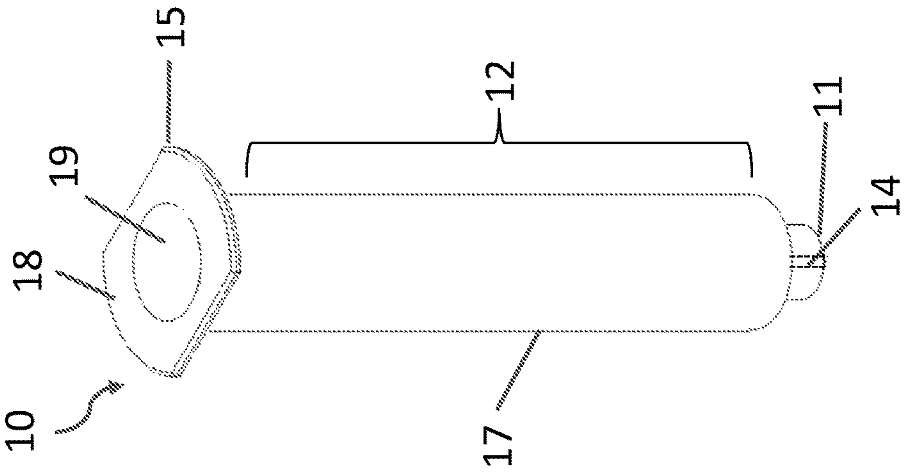
FIG. 2 is a perspective view of an exemplary syringe body of the exemplary syringe of FIGS. 1A-1D in some embodiments.

In some embodiments, the exemplary syringe body 10 comprises a barrel flange 18 on the proximal end 15. As shown in FIG. 2, the barrel flange 18 may include two edges in parallel lines and other two edges in concentric lines in some embodiments.

The syringe body 10 includes a barrel flange 18 on the distal end, a Luer Lock or slip tip on the proximal end, and a barrel where the contents of the syringe are stored. The contents of the syringe are held in place by a movable stopper on the distal end and a Luer Lock or slip tip cap or other existing art on the proximal end. The tip of the syringe body may or may not contain geometry making it compatible with the Luer Lock system. The inclusion or exclusion of this feature has no effect on the rest of the design.

Figure 3:
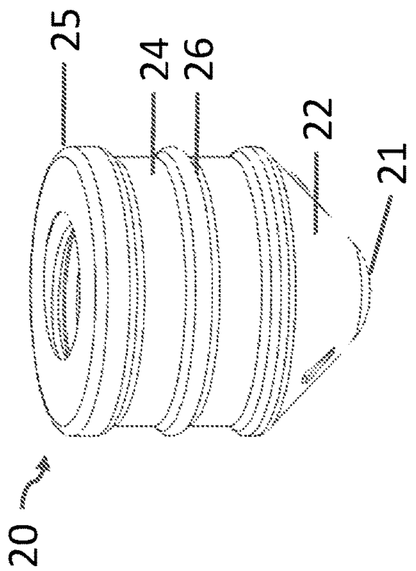
FIG. 3 is a perspective view of an exemplary stopper of the exemplary syringe of FIGS. 1A-1D in some embodiments.

As illustrated in FIGS. 1A-1D, the stopper 20 is disposed inside the barrel 12 and is configured to seal the interior volume 13. As shown in FIG. 3, in some embodiments, the stopper 20 has a tip 22 at its proximal end or portion 21 (or called the first end or portion), and a proximal end or portion 25. The stopper 20 has a tube-shaped middle section 24, which may include with screw marks 26. The proximal portion 25 of the stopper 20 may also define a hole with screw marks for attaching the stopper insert 30.

The stopper 20 can be made of any suitable elastic material. Examples of a suitable material include, but are not limited to, rubber, TPE, TPV, and any other elastomers. The stopper 20 is an elastic cylindrical component that maintains a vacuum tight seal while the syringe is in transport and while the syringe is used for administration. In existing technologies, a stopper is directly fixed to a plunger rod and is not detached or assembled during use.

Figure 4:
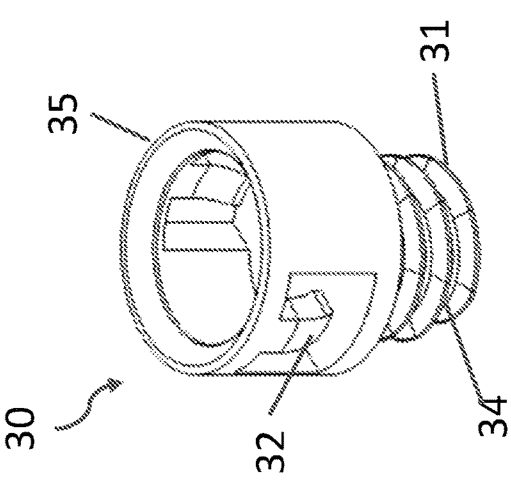
FIG. 4 is a perspective view of an exemplary stopper insert of the exemplary syringe of FIGS. 1A-1D in some embodiments.

Referring to FIG. 4, the stopper insert 30 has a distal portion 31 and a proximal portion 35. The distal end of the stopper insert 30 interfaces with the stopper 20, which may be a rubber stopper. It may interface with the stopper 20 through a flange that is inserted or twisted into the rubber stopper to secure it in place. The proximal end 35 of the stopper insert 30 interfaces with the proximal end of plunger rod 40. The proximal end 35 may contain a circular hole that accepts the proximal end of the plunger rod 40 in any radial orientation. The proximal end 35 may include a cantilever arm snap feature, which can flex during installation of the plunger rod.

In some embodiments, the distal portion 31 includes screw features 34, which match with the screw marks in the proximal portion 25 of the stopper 20. The stopper insert 30 is a connecting fixture piece or device that secures the plunger rod 40 to the stopper 20 when the syringe 100 is assembled. The proximal portion 35 includes a fixture that interfaces with the plunger rod 40. Multiple embodiments are described in the present disclosure. Referring to FIG. 4, the proximal portion 35 of the stopper insert 30 comprises one or more cantilever arm 32. This configuration is for illustration only. Other configurations as described herein can be used.

The cantilever arm is oriented such that the raised lip on the proximal end of the plunger rod is able to slide past the wedge during installation, but the cantilever arm flexes back to its original position when the plunger rod is fully seated, which prevents the plunger rod from easily becoming uninstalled.

The stopper insert 30 can be made of any suitable material. Examples of a suitable material include, but are not limited to, a rubber, a thermoplastic elastomer (TPE), polypropylene, and polyethylene. The stopper insert 30 may be made of rigid plastics or a relatively rigid elastomer in some embodiments.

Referring to FIGS. 1A-1D, the stopper insert 30 is disposed inside the barrel 12 and coupled with the stopper 20 at the distal portion of the stopper insert 30. The stopper 20 and the stopper insert 30 are put into the syringe body 10 from the second opening 19 of the syringe body 10, and are located toward to the second opening 19 (or the proximal end 15).

The plunger rod 40 is disposed outside the syringe body 10. The plunger rod 40 is stored on the side of the syringe body 10 during transit. To administer the contents of the prefilled syringe, the user must separate the plunger rod 40 from the syringe body 10 and install it into the stopper insert 30.

Figure 5:
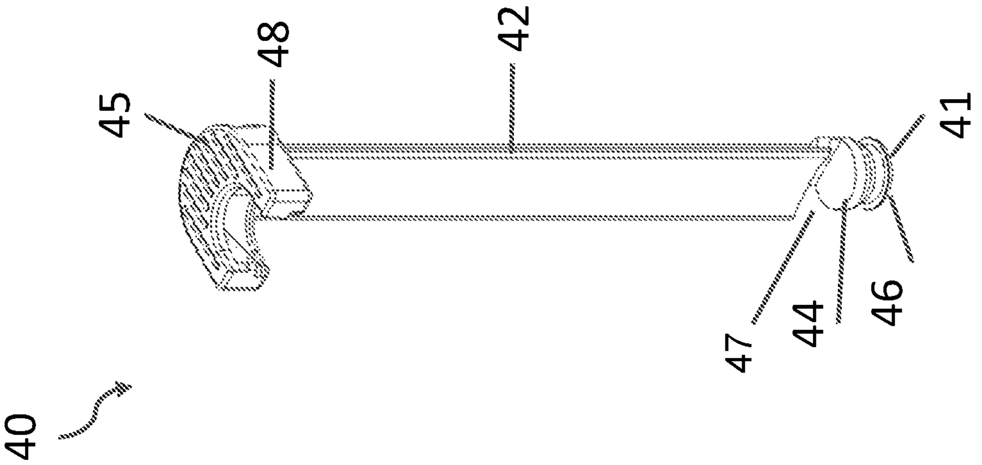
FIG. 5 is a perspective view of an exemplary plunger rod (or a plunger device) of the exemplary syringe of FIGS. 1A-1D in some embodiments.

Referring to FIG. 5, an exemplary plunger rod 40 in accordance with some embodiments is illustrated. The plunger rod 40 has a first end (proximal end) 41, a second end (distal end) 45, and a middle section 42. The middle section 42 is disposed along the barrel wall 17 of the barrel 12 (FIGS. 1A-1D). The first end 41 of the plunger rod 40 is sized and configured to be coupled with the stopper insert 30 at the proximal portion 35 of the stopper insert 30 before the syringe 100 is assembled and used.

The second end 45 of the plunger rod 40 is reversibly attached to the distal end 11 or the proximal end 15 of the syringe body 10. As illustrated in FIGS. 1A-1D, in some embodiments, the second end 45 of the plunger rod 40 is reversibly attached to the distal end 11 of the syringe body 10. This configuration in FIGS. 1A-1D is for illustration purposes only. In some embodiments, the second end 45 of the plunger rod 40 comprises a flange 48, which is configured to attach the plunger rod 40 to the syringe body 10. The flange 48 may have a patterned surface. The flange 48 is configured to be easily engaged with a user after the syringe 100 is assembled. The user can put a finger such as a thumb onto such a patterned surface so as to push the plunger rod 40 and push a therapeutic product inside the syringe out during operation.

The plunger rod 40 is configured to be detached and assembled with the stopper insert 30 by a user so as to drive the stopper 20 in a direction from the proximal end 15 to the distal end 11 of the syringe body 10 or from the second opening 19 to the first opening 14 of the syringe body 10.

In some embodiments, the middle section 42 of the plunger rod 40 has a wall with a curved surface matching with a portion of an exterior surface of the barrel wall 17. The middle section 42 of the plunger rod 40 is proximal to or in contact with the portion of an exterior surface of the barrel wall 17. The middle section 42 may be a portion of a cylindrical shape. The plunger rod body is crescent shaped such that it has enough strength to dispense the contents of the syringe without buckling but also lays flush with the body of the syringe. The crescent shape follows the contour of the syringe body.

The distal end 45 of the plunger rod 40 have thumb interface/plunger flange 48. The flange 48 may include a semi-circular cutout to nest against the distal end of the syringe body during storage and transport. Semi-circular cutout contains static features that provide slight resistance during installation and prevent the plunger rod from falling off the syringe body from the force of gravity. The flange 48 includes enough surface area thereon for a user to comfortably depress or pull the plunger rod 40 with a thumb or other finger(s) without irritation.

The flange 48 may also contain raised grooves on the top of the plunger rod, and the grooves help provide traction when pushing the plunger rod 40 so the user's finger is less likely to slide or slip off of the plunger flange.

The proximal end 41 of plunger rod 40 includes a stopper insert interface. For example, the proximal end 41 of the plunger rod 40 may include a raised lip to interface with the cantilever arm snap feature on the stopper insert. The raised lip allows the cantilever arm snap feature on the stopper insert to slide past easily in the installation direction, but the raised lip prevents the cantilever arm snap feature on the stopper from sliding back over once it is installed. This secures the plunger rod in place after installation.

Figure 6B:
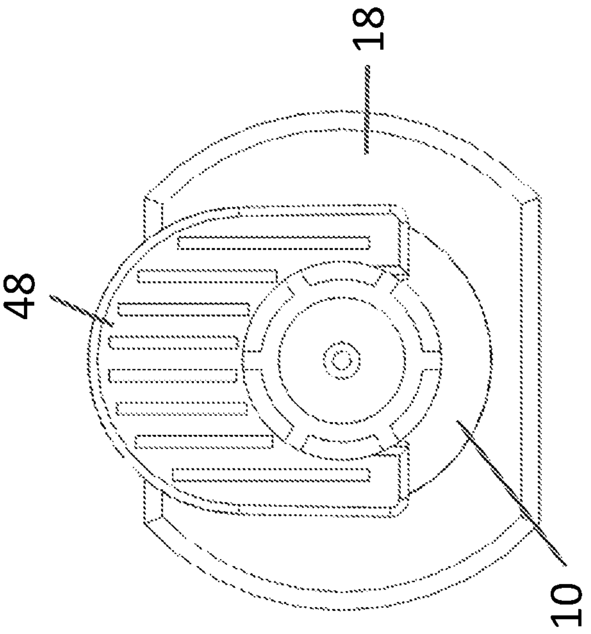
FIG. 6B is a plan view of the exemplary syringe of FIGS. 1A-1D at an end of a second direction (at a proximal end) in some embodiments.
Figure 6A:
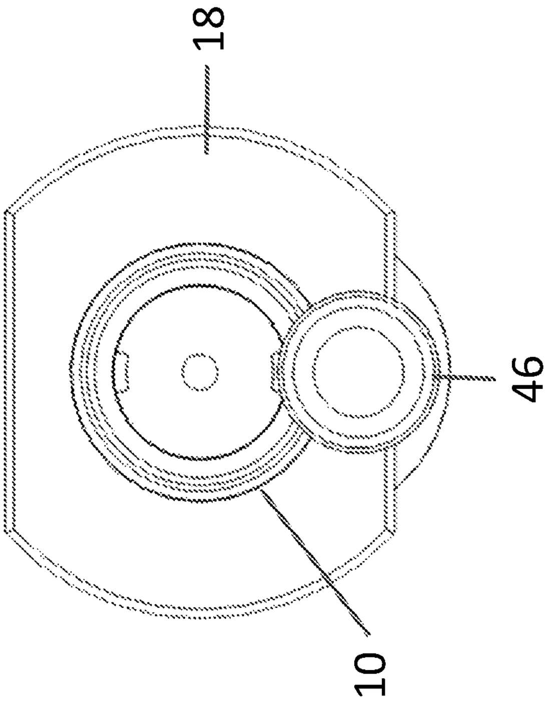
FIG. 6A is a plan view of the exemplary syringe of FIGS. 1A-1D at an end of a first direction (at a distal end) in some embodiments.

In some embodiments, the plunger rod 40 comprises a snap cylinder 44 and defines a concave portion 47 between the snap cylinder 44 and the middle section 42. The concave portion 47 is configured to receive a portion of the barrel flange 18 of the syringe body 10 (FIGS. 1A-1D and FIG. 5). The plunger rod 40 may also have a raised lip 46. FIGS. 6A and 6B illustrate the exemplary syringes of FIGS. 1A-1D at a distal end and at the proximal end, respectively, in some embodiments.

The snap cylinder 44 increases the surface area in contact with the stopper insert and provides stability in the installed state relative to the stopper. The snap cylinder 44 matches the shape of the stopper insert 30, so the user can install it in any orientation. The snap cylinder 44 rests on top of the barrel flange 18 of the syringe body 10, when the plunger rod is nested against the syringe body 10, preventing axial and radial movement of the plunger rod relative to the syringe body.

The plunger rod 40 can be made of any suitable rigid material. Examples of a suitable material include, but are not limited to, propylene and polyethylene.

During the assembly stage, in some embodiments, the proximal end 41 of the plunger rod 40 may be connected to the proximal end 35 of the stopper insert or directly to the proximal end 25 of the stopper 20. This connection method is described through multiple embodiments in the present disclosure. The proximal end 41 of the plunger rod 40 contains a fixture that may interface with a component of the stopper insert 30 or a component of the stopper 20. The distal end of the plunger rod 40 includes a fixture such as a flange 48 that interfaces with the syringe body 10.

Figure 7:
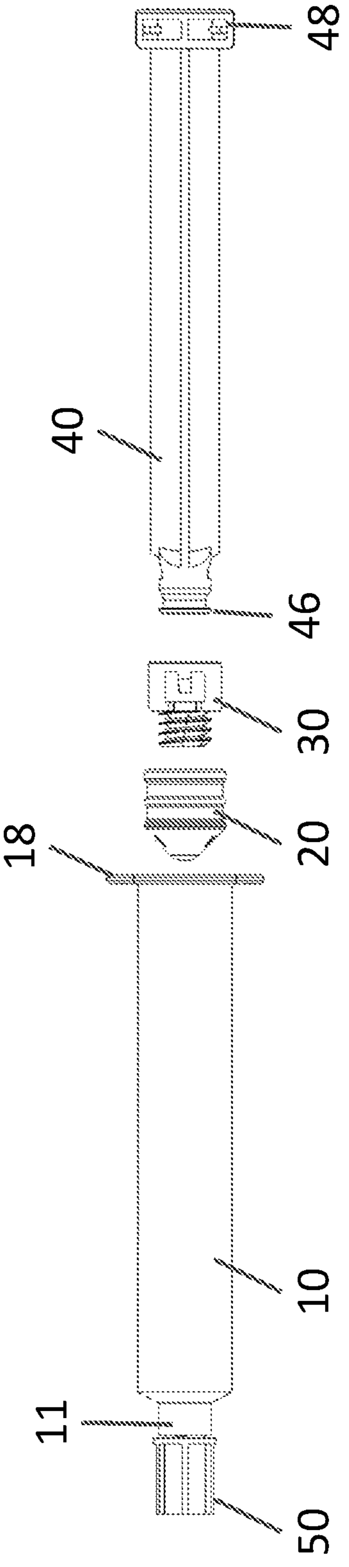
FIG. 7 is an exploded and plan view of the exemplary syringe of FIGS. 1A-1D being assembled in accordance with some embodiments.
Figure 8A:
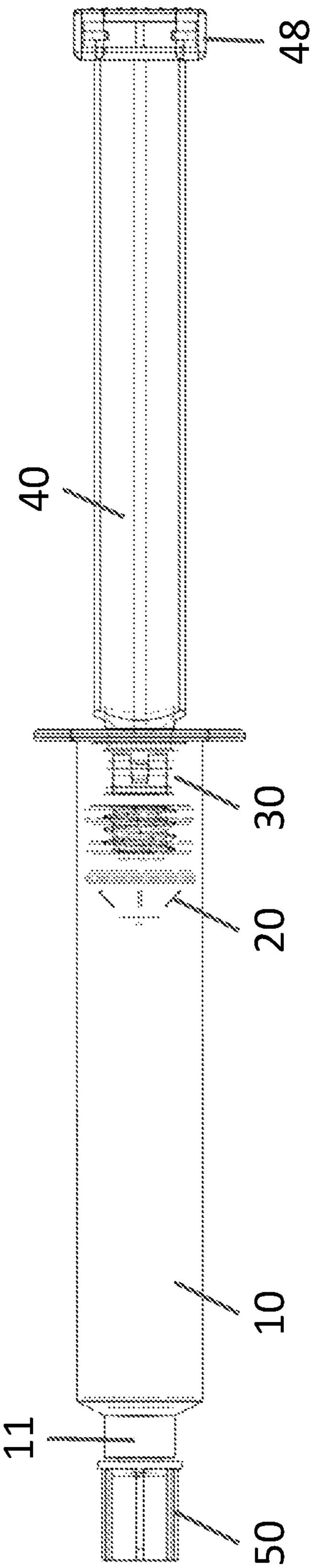
FIGS. 8A-8B are side plan views of the exemplary syringe of FIGS. 1A-1D after being assembled in accordance with some embodiments.
Figure 8B:
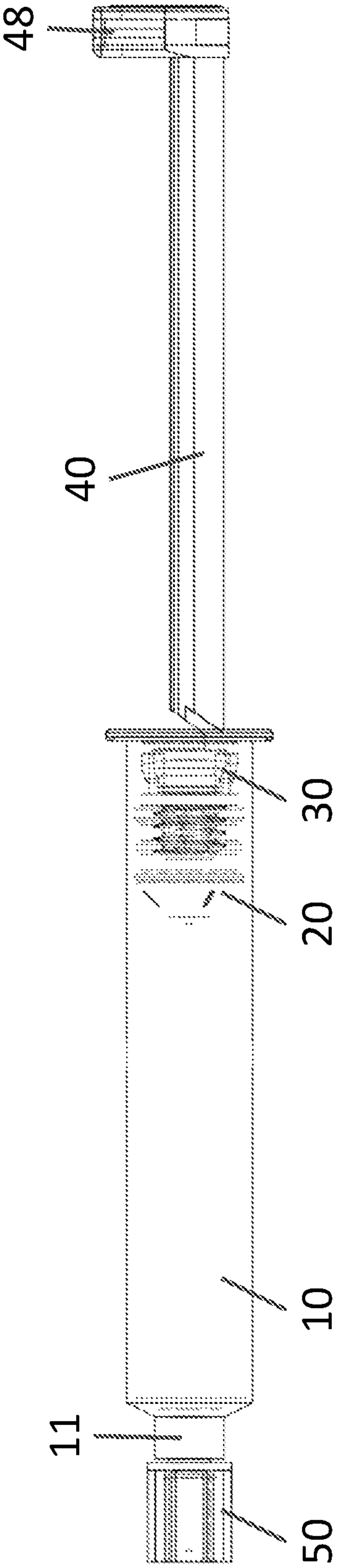
Figure 10:
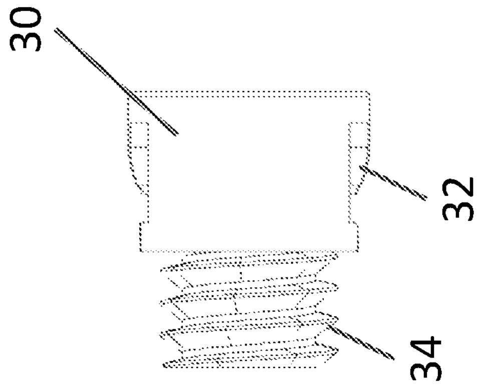
FIG. 10 is a perspective view of the exemplary stopper insert of FIG. 4.
Figure 11:
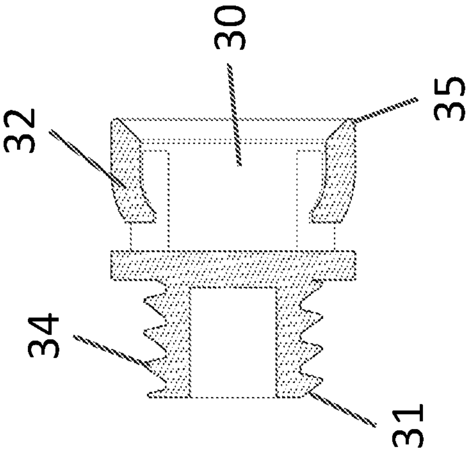
FIG. 11 is a sectional view of the exemplary stopper insert of FIG. 4 in accordance with some embodiment.
Figure 9:
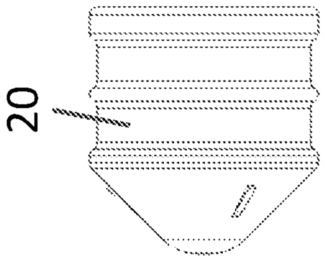
FIG. 9 is a perspective view of the exemplary stopper of FIG. 3.

Referring to FIG. 7, an exploded and plan view of the exemplary syringe 100 described in FIGS. 1A-1D being assembled is illustrated. FIGS. 8A-8B are side plan views of the exemplary syringe 100 after assembled in accordance with some embodiments.

In some embodiments, during sterilization, shipping, storage, and distribution, the plunger rod 40 stays stored and clipped securely to the side of the syringe barrel. During sterilization, shipping, storage, and distribution, the proximal end of the plunger rod 40 clips to the barrel flange and the distal end of the plunger rod 40 clips to the tip of the syringe. To use the syringe, the plunger rod 40 is fully removed from the side of the syringe. Then, the proximal end of the plunger rod 40 is fit into an opening in the back of the stopper insert and installed into the back of the stopper insert using press-fit. Once installed into the back of the stopper insert, the plunger rod 40 is firmly attached to the stopper insert 30. The distal end of the plunger rod 40 becomes a surface for the thumb to depress against (plunger flange) to expel the syringe contents. The distal end of the plunger rod 40 can also be pulled to draw contents into the syringe. The designs descried herein also maintain the core function of the drug delivery method of the syringes.

Referring to FIGS. 9-11 and 12A and 12B, an exemplary stopper 20 and an exemplary stopper insert 30 are used for the syringe 100 in accordance with some embodiments. Such an exemplary stopper 20 and such an exemplary stopper insert 30 are used to form a mechanical interlock through a snap mechanism as illustrated in FIGS. 13A-13B.

Figure 12B:
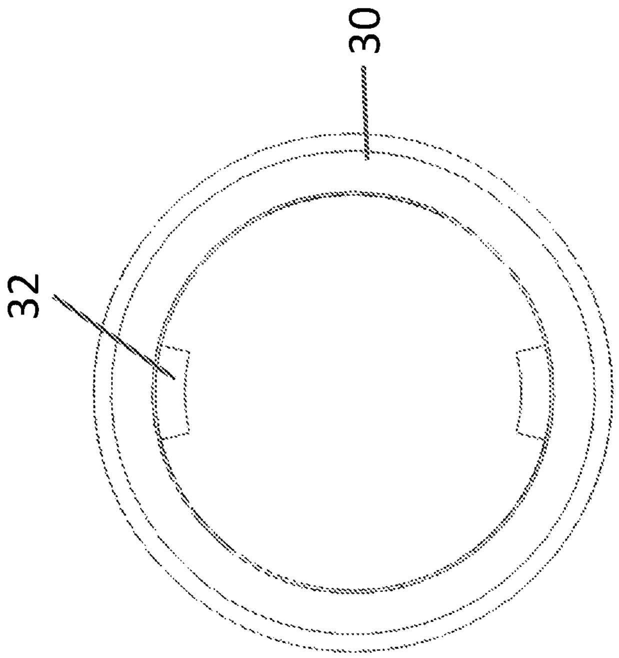
FIG. 12B is a plan view of the exemplary stopper insert at its second end (the proximal end) in accordance with some embodiments.
Figure 12A:
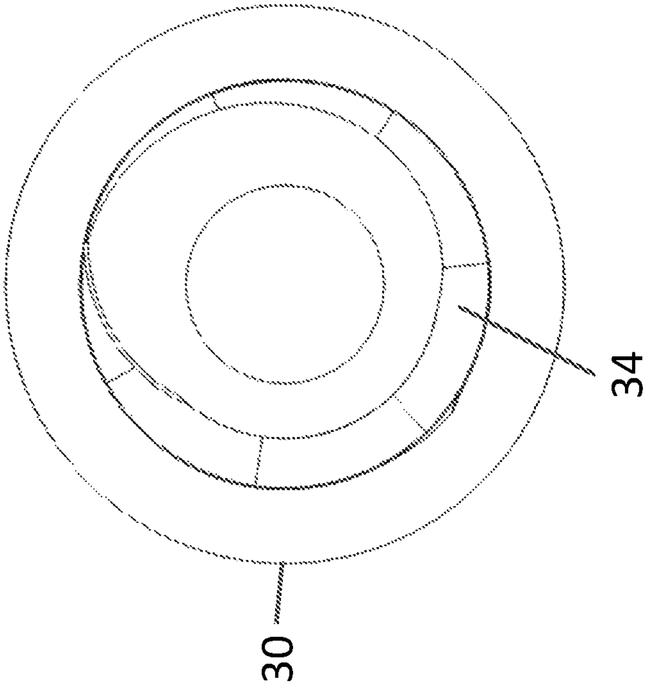
FIG. 12A is a plan view of the exemplary stopper insert at its first end (the distal end) in accordance with some embodiments.
Figure 13B:
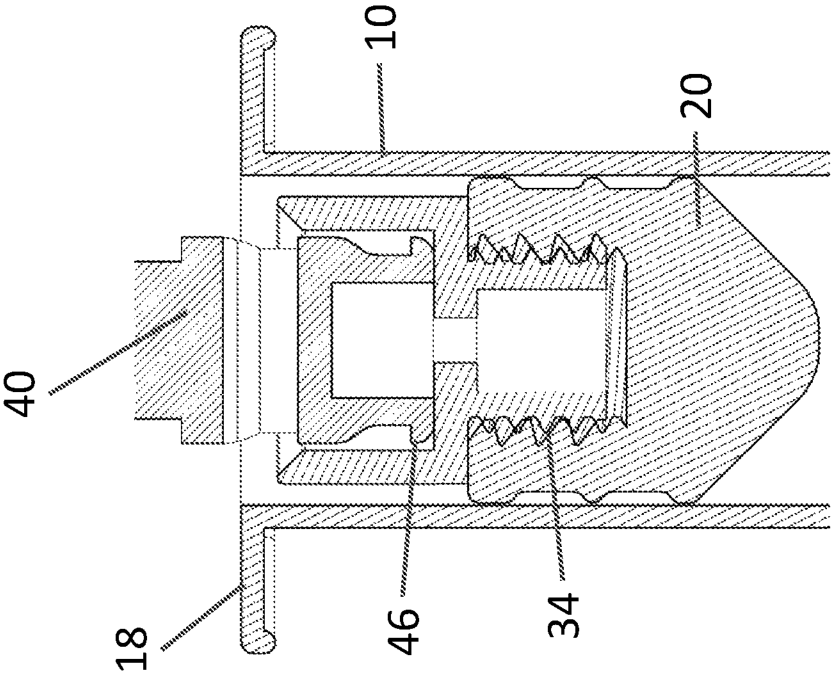
FIGS. 13A-13B are sectional plan views illustrating that the exemplary plunger rod is assembled with the exemplary stopper insert and the exemplary stopper through a snap mechanism in accordance with some embodiments.
Figure 13A:
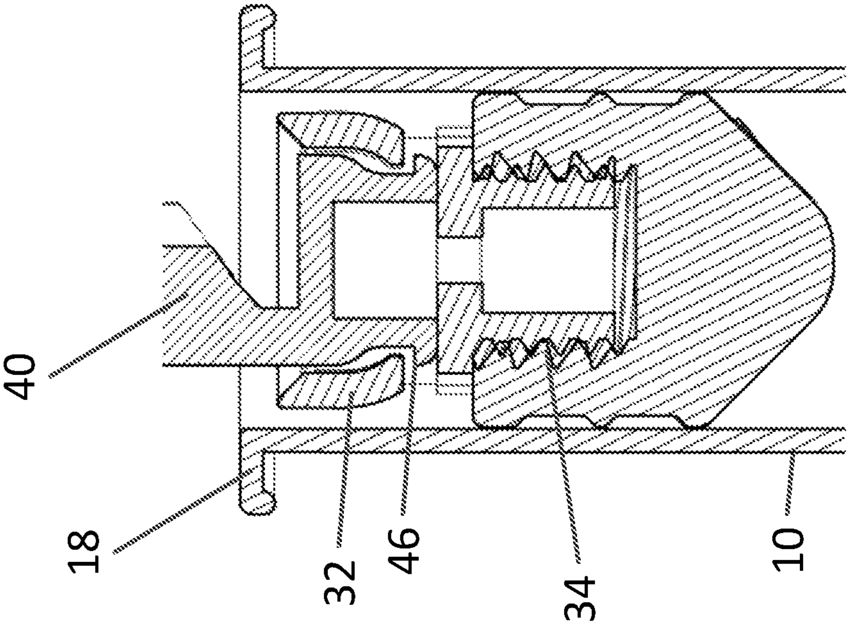

As described in FIG. 4, in some embodiments, the proximal portion 35 of the stopper insert 30 comprises one or more cantilever arms 32, and the distal portion 31 of the stopper insert 30 includes screw features 34 (FIGS. 10-11 and 12A-12B). FIGS. 12A and 12B are plan view of the exemplary stopper insert 30 at its distal end and its proximal end, respectively. The screw features 34 match with the screw marks in the proximal portion 25 of the stopper 20 (FIG. 4 and FIG. 9) when the stopper insert 30 is connected with the stopper 20.

Figure 14:
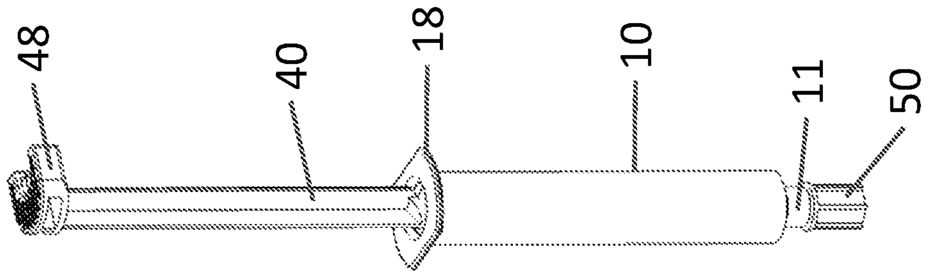
FIG. 14 is a perspective view of an exemplary assembled syringe in accordance with some embodiments.
Figure 15B:
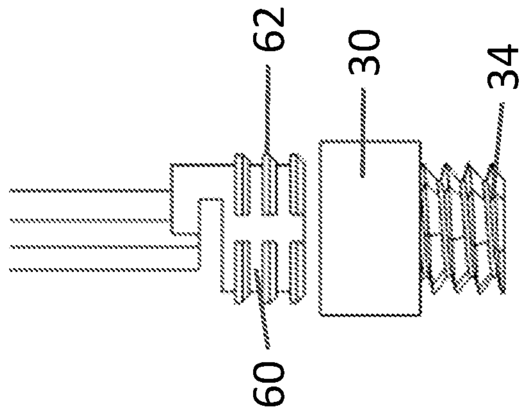
FIGS. 15A-15C are side plan views illustrating a second exemplary plunger rod and a second exemplary stopper insert in accordance with some embodiments.
Figure 15A:
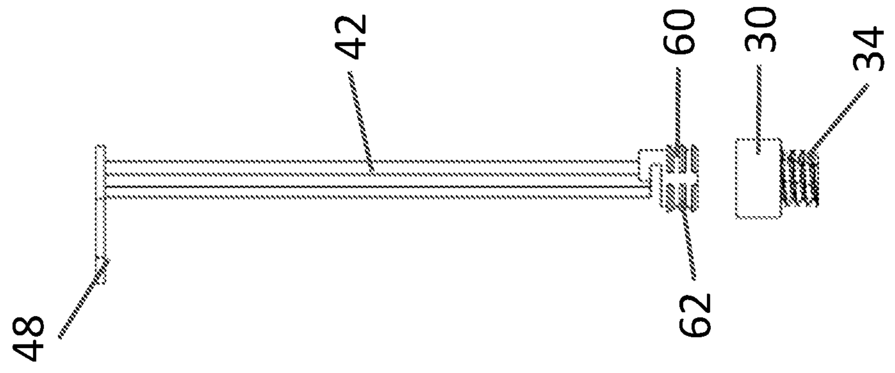
Figure 15D:
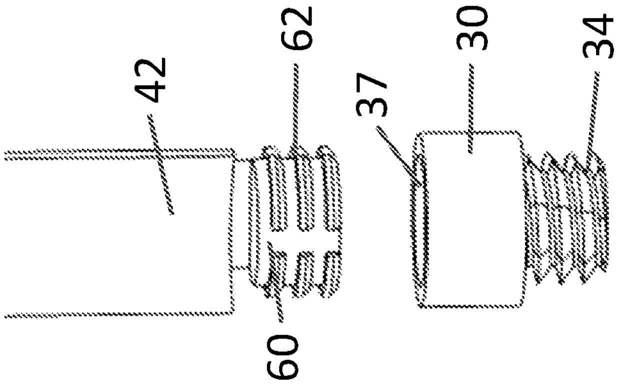
FIG. 15D is a perspective view illustrating the exemplary plunger rod and the exemplary stopper insert shown in FIGS. 15A-15C.
Figure 15C:
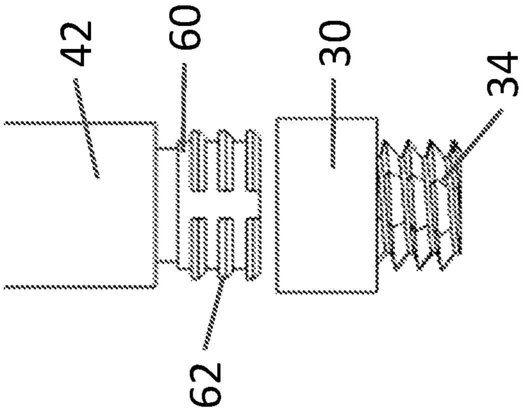

In some embodiments, the first end of the plunger rod 40 comprises a raised lip 46. Referring to FIGS. 13A-13B, the raised lip 46 is configured to form a mechanical interlock with the cantilever arms 32 in the stopper insert 30 through a snap mechanism. The cantilever arms 32 may be configured to expand slightly when the plunger rod 40 is pushed into the stopper insert 30, and then locks the raised lip 46 in place. The raised lip 46 cannot be pulled out after assembled. FIGS. 13A-13B are sectional plan views illustrating the same assembly but in different cross-sections. FIG. 14 is a perspective view of an exemplary assembled syringe in accordance with some embodiments.

Besides the mechanism illustrated in FIGS. 9-11, 12A-12B, and 13A-13B, there are other alternative embodiments with different locking mechanisms between the stopper insert 30 and the plunger rod 40. For example, in some embodiments, the plunger rod can be turned by an angle such as approximately, more than or less than a 90 degree in the stopper insert to lock the plunger rod into the stopper insert. It may be similar to a "key style" insertion technique.

For another example, in some embodiments, there is a non-permanent connection between plunger rod and stopper insert. The stopper insert contains no snap feature, no bridge, or no wedge. The stopper insert is able to slide freely from the installed position to the uninstalled position without any locking feature.

For another example, in some embodiments, permanent connection can be formed between plunger rod and stopper insert. The plunger rod is firmly locked into place with a more robust locking feature on the stopper insert such that removal of the plunger rod would require the parts to mechanically fail.

For another example, in some embodiments, force-fit connection can be formed without threads. The plunger rod and the stopper insert connect using a friction fit, whereby the plunger rod encounters an equal resistance to install as it does to uninstall which results from compression of the two parts or friction between the two parts.

For another example, in some embodiments, an interlocking connection can be formed through female threads on the stopper insert and male threads on plunger rod (screw together). The stopper insert contains female threads that fit with male threads on the plunger rod and installation involves screwing the plunger rod onto the stopper insert.

For another example, in some embodiments, an interlocking connection can be formed through male threads on the stopper insert and female threads on the plunger rod (screw together). The stopper insert contains male threads that fit with female threads on the plunger rod and installation involves screwing the plunger rod onto the stopper insert.

For another example, in some embodiments, cross peg on plunger rod fits into a cross hole in the stopper insert. The stopper insert contains a cross-shaped keyhole, which is the same shape as the proximal end of the plunger rod. The plunger rod is inserted into the stopper insert and then rotated such that the arms of the cross are no longer in alignment with the cross-shaped keyhole of the stopper insert, preventing axial removal of the plunger rod without subsequent rotation and alignment of the arms of the cross.

For another example, the stopper insert includes the bridge and wedge features, which are oriented such that the snap occurs during axial installation with shapes other than a circle. Such other shapes may be a square, triangle, pentagon, diamond, hexagon, or any other shape.

FIGS. 15A-15D, 16A-16C, and 17A-17B illustrate three additional embodiments. Except the different structures described herein, all other structure features are the same as described above.

Referring to FIGS. 15A-15D, in some embodiments, the proximal portion 35 of the stopper insert 30 is flexible and having threads 37 therein. The first end 41 of the plunger rod 40 comprises a barb structure 60 having angular edged structures 62 (barbs). The bard structure 60 is rigid. Similar to the snap cylinder 44, the barb structure 60 also has a cylindrical shape with the angular edged structure 62 thereon. The barb structure 60 is configured to be inserted into and lock with the proximal portion 35 of the stopper insert 30 through the angular edged structures 62 inside the threads 37. The rigid barb can be pushed into the flexible hose and form a secure fit due to the shape of the barbs. A barbed hose connection can be formed between the plunger rod and the stopper insert. The stopper insert contains a short, flexible cylinder which can expand when the proximal end of the plunger rod is inserted. The proximal end of the plunger rod contains a series of barbs that allow for easy insertion but difficult removal.

Figure 16C:
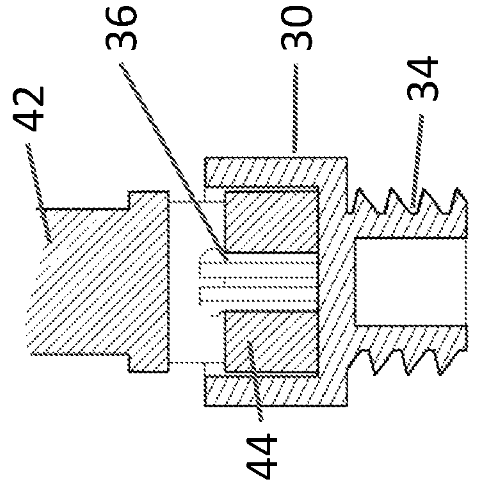
FIG. 16C is a sectional view illustrating the exemplary plunger rod and the exemplary stopper insert shown in FIG. 16A after assembled together through another snap fit mechanism.
Figure 16B:
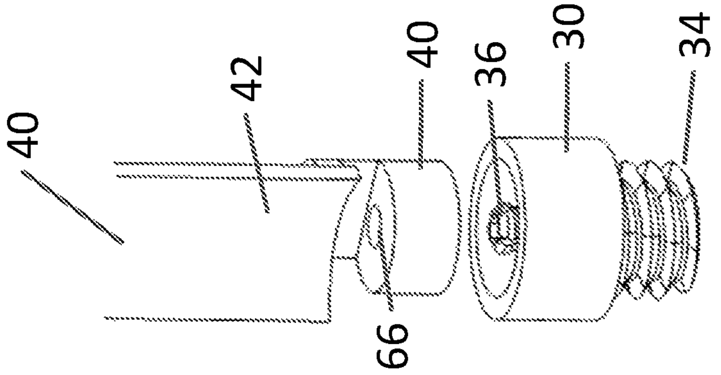
FIG. 16B is a perspective view illustrating the exemplary plunger rod and the exemplary stopper insert shown in FIG. 16A.
Figure 16A:
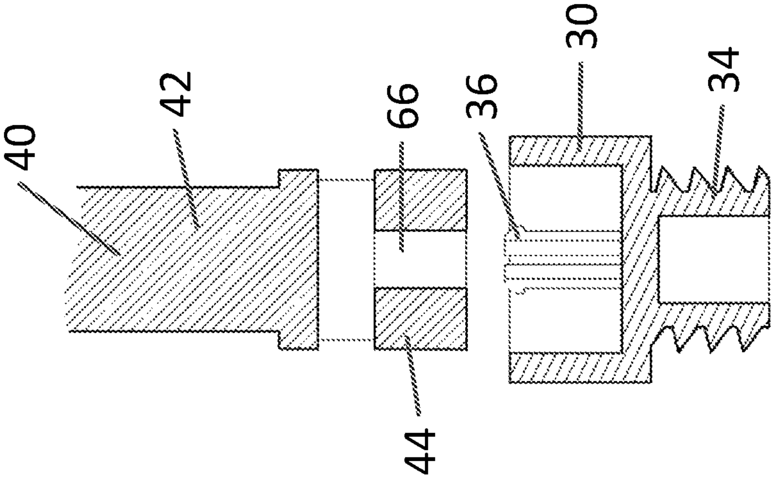
FIG. 16A is a sectional view illustrating a third exemplary plunger rod and a third exemplary stopper insert in accordance with some embodiments.

Referring to FIGS. 16A-16C, in some embodiments, the proximal portion 35 of the stopper insert 30 comprises a protrusion 36 in a middle and defines a trench around the protrusion 36. The first end 41 of the plunger rod 40 defines a hole 66. The first end of the plunger rod 40 is configured to be disposed in the trench, and the protrusion 36 is configured to be disposed inside the hole to provide a male/female interlocking structure. In this alternative Embodiment, the protrusion is a radial tower structure for snapping into the stopper insert 30. The snap features are in the middle of the stopper insert. The plunger rod has a hole in the end to interface with the snap tower in the stopper insert. Shown in section view and isometric, the support wall wraps all the way around the snap feature, ensuring a snug fit.

Figure 17B:
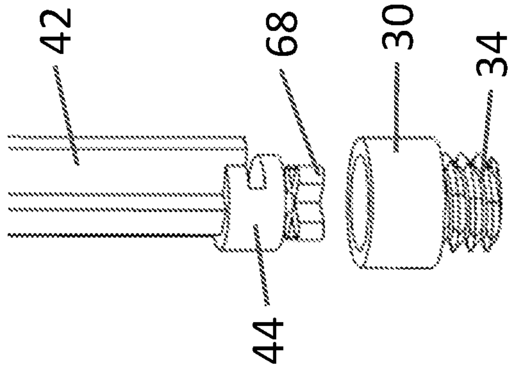
FIGS. 17A-17B are perspective views illustrating a fourth exemplary plunger rod and a fourth exemplary stopper insert in accordance with some embodiments.
Figure 17A:
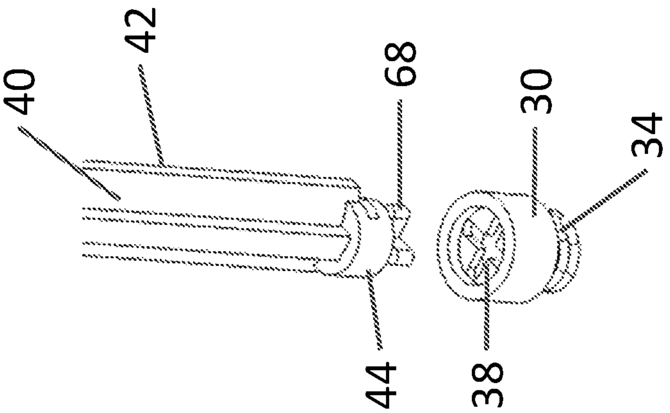

Referring to FIGS. 15A-15D, in some embodiments, the first end 41 of the plunger rod 40 comprises a patterned tip structure 68. For example, in some embodiments, such a patterned tip structure 68 has a shape of capitalized “X” as illustrated in FIGS. 17A-17B. The proximal portion 35 of the stopper insert 30 defines a patterned depression 38 having a shape complimentary to the patterned tip structure. For example, in some embodiments, such a patterned depression has a shape of capitalized “X” as illustrated in FIG. 17A. The first end of the plunger rod 40 is configured to be twistedly fitted into the proximal portion 35 of the stopper insert 30 through these protrusion and depression structure. In this alternative embodiment, the plunger rod has an “X” shape that fits in the “X” shaped hole in the stopper insert. After the plunger rod is fully inserted, it can be twisted in order to prevent the “X” from sliding out during use.

In some embodiments, the stopper insert 30 has a flexible membrane with a series of cuts in an X shape that allow for the insertion of the proximal end of the plunger rod 40. The proximal end of the plunger rod 40 contains a flange that can be inserted into the stopper insert 30 through the flexible membrane, but it has to be done at an angle.

In some embodiments, the second end 45 of the plunger rod 40 comprises a plunger flange 48 configured to be reversibly attached to the distal end or the proximal end of the syringe body. In some embodiments, the second end of the plunger rod is attached to the distal end of the syringe body. In some embodiments, the second end of the plunger rod is attached to the proximal end of the syringe body.

As described in FIG. 5, the second end 45 of the plunger rod 40 may include a flange 48. The flange 48 illustrated in FIG. 5 includes a notch, for example, in a semi-circular shape. In addition to this configuration, the plunger rod may have other alternative structures for attaching the plunger rod to the syringe body.

Figure 18B:
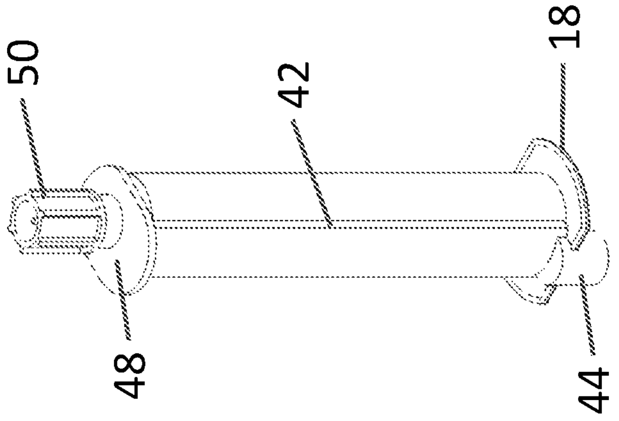
FIG. 18B is a perspective view illustrating the fifth exemplary plunger rod disposed outside an exemplary syringe body in some embodiments.
Figure 18A:
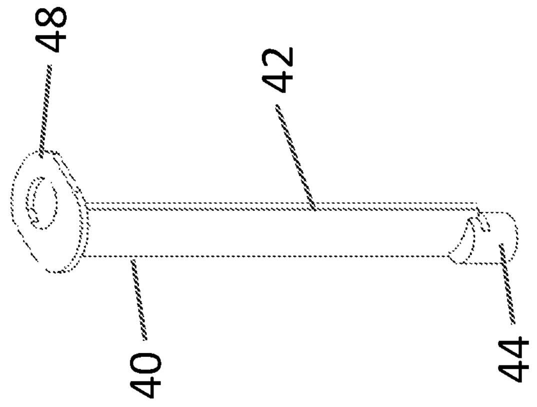
FIG. 18A is a perspective view illustrating a fifth exemplary plunger rod in accordance with some embodiments.
Figure 19A:
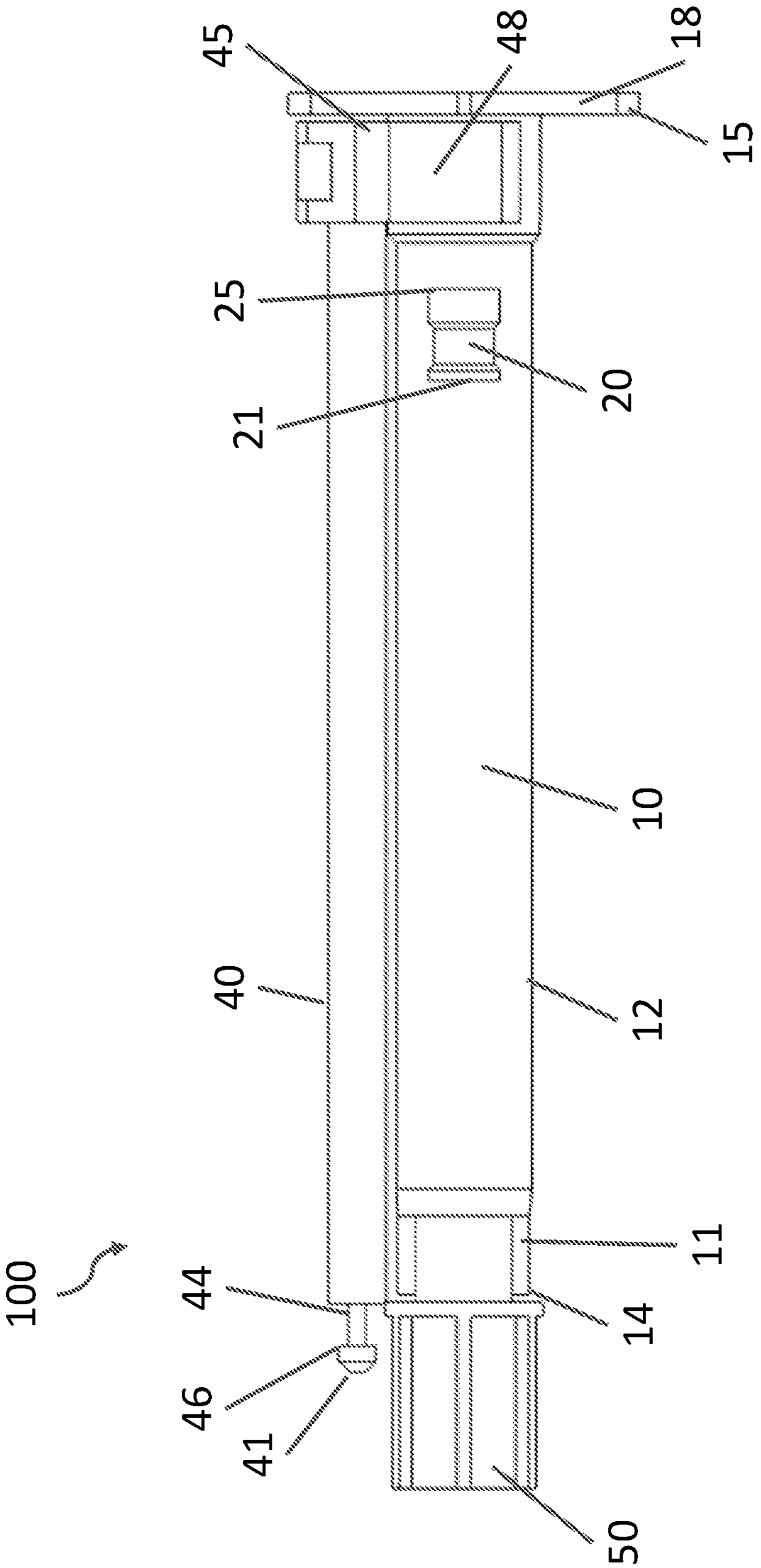
FIGS. 19A-19D are side plan views illustrating another exemplary syringe, in which an exemplary plunger rod is coupled with the proximal end of the exemplary syringe, in accordance with some embodiments.
Figure 19B:
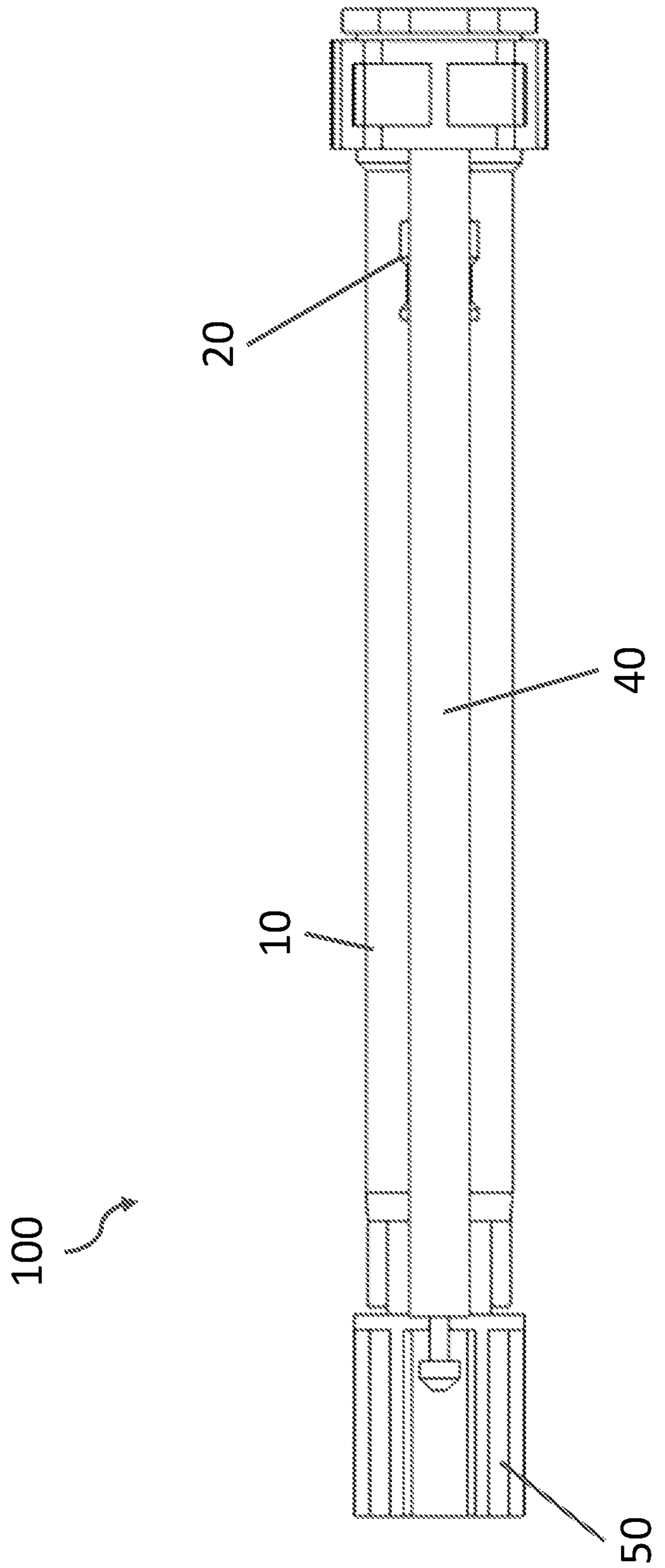
Figure 19C:
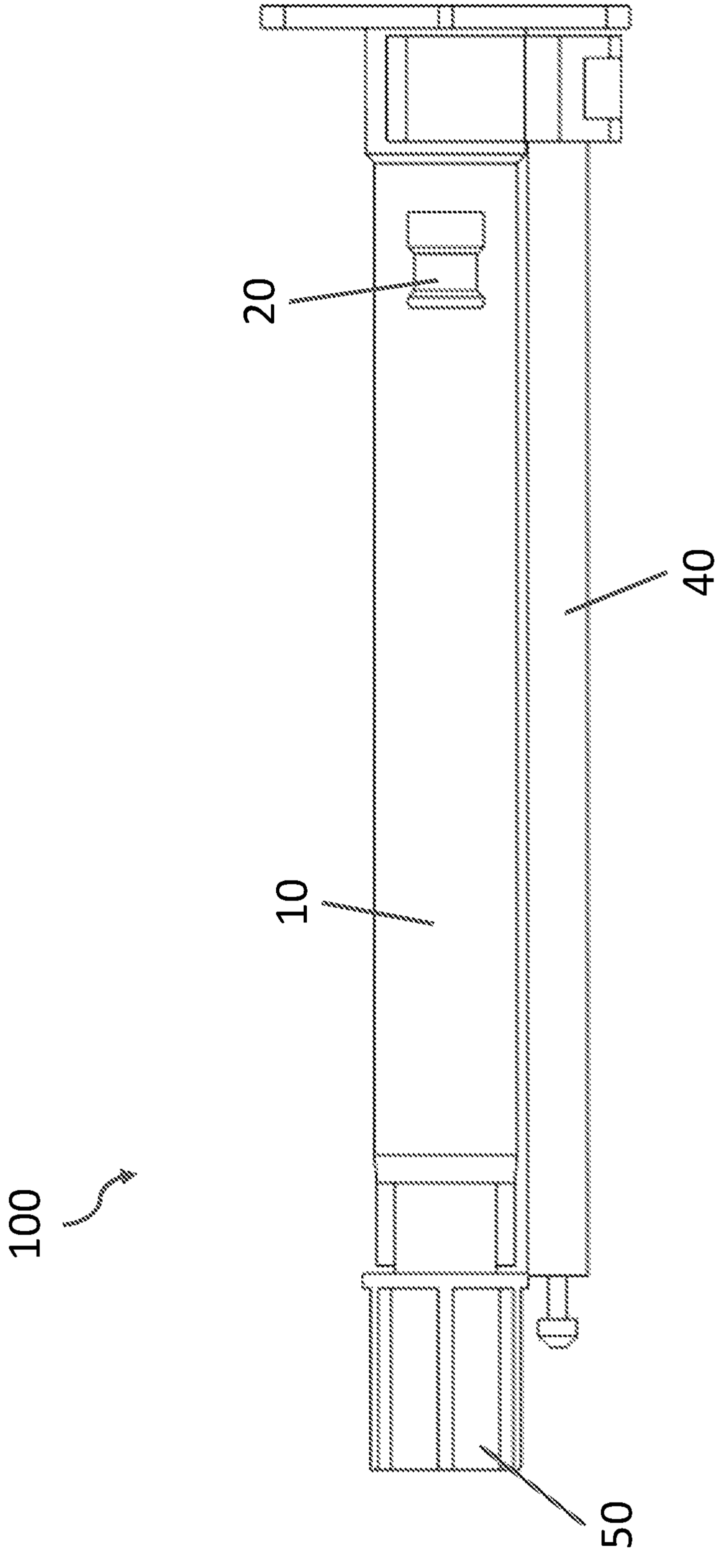
Figure 19D:
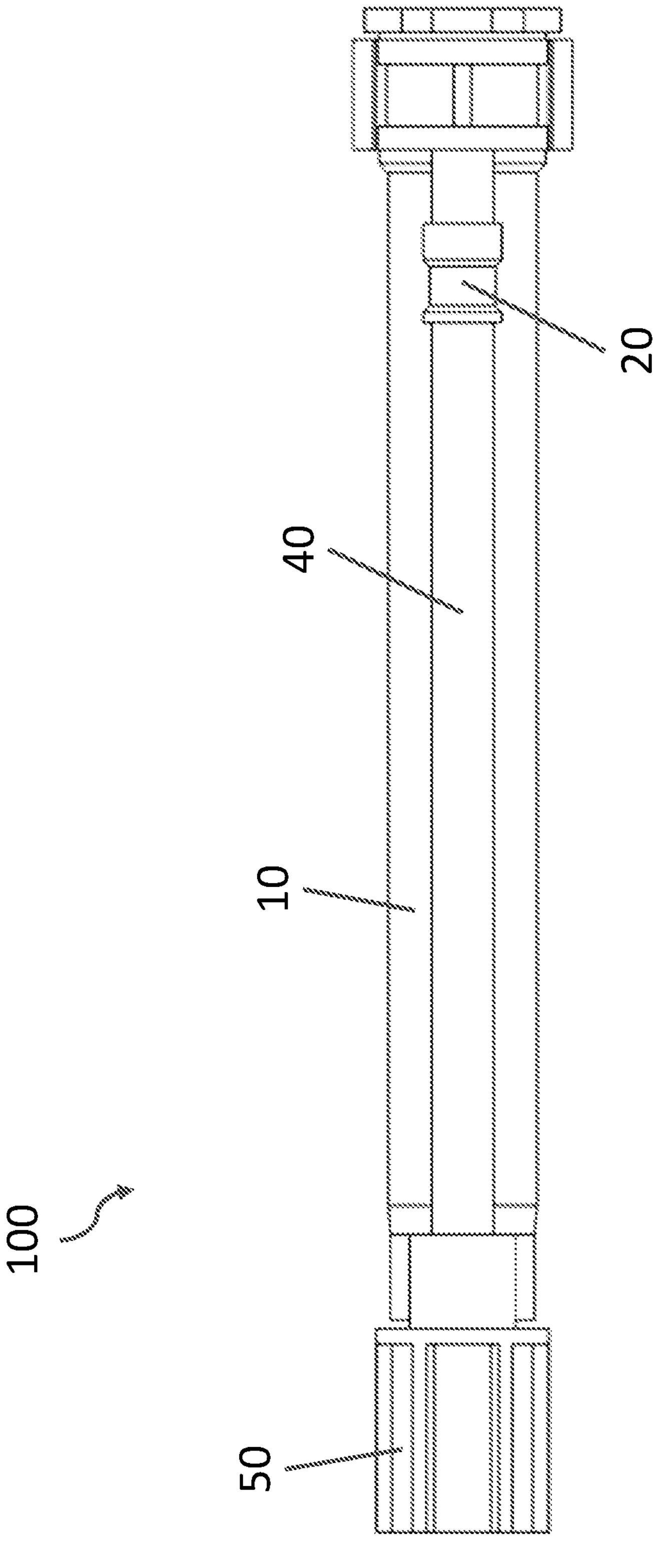

Referring to FIGS. 18A-18B, In some embodiments, the plunger flange 48 at the second end of the plunger rod 40 defines a hole. The second end of the plunger rod 40 is attached to the distal end 11 of the syringe body 10. The distal end 11 of the syringe body 10 is disposed through the hole. In this alternative embodiment, the plunger rod 40 is attached to the syringe body through circular attachment. The plunger rod 40 is attaches to the syringe barrel via an enclosed circle, looping over the top of the tip of the syringe.

FIGS. 19A-19D are side plan views illustrating another exemplary syringe 100, in which an exemplary plunger rod 40 is coupled with the proximal end 15 of the syringe body 10, in accordance with some embodiments. The flange 48 is coupled with the proximal end 15 of the syringe body 10. In this alternative embodiment, the distal end of the plunger rod 40 contains a circular cutout that is large enough to fully encase the syringe body. The fully circular hole on the thumb depressor/plunger flange 48 loops all the way around the syringe.

The distal end of the plunger rod during storage may also be attached to an entity that is attached to the syringe body instead of attaching directly to syringe body. In some embodiments, the plunger rod doubles as the Luer Lock cap, slip tip cap, or other type of cap, attaching to the tip of the syringe body for storage.

In some embodiments, the syringe body contains a rail that the plunger rod can interface with. The plunger rod can slide along the rail to install. Once installed, the only way to remove the plunger rod is to axially slide the plunger rod along the rail. The plunger rod has features that capture the rail such that the plunger rod cannot simply fall off the rail after it is slid axially down the length of the rail.

In some embodiments, the stopper is attached directly to the plunger rod. At the proximal end of the plunger rod, there exists a hinge that is formed by thin walls of joined plastic. When the hinge is open so that the two pieces are collinear, the plunger rod extends along the body of the syringe and can be secured to the syringe body at the distal end. To install the device, the hinge is closed and the walls have male and female features to secure the plunger rod in place for injection.

The plunger rod and stopper insert connection design and interface described in this application could also be utilized in other contexts outside that of a syringe, including outside of the healthcare industry. This design and interface could be utilized to semi-permanently connect a variety of items.

In some embodiments, the syringe 100 is a prefilled syringe, which comprises a therapeutic product disposed inside a portion of the interior volume between the distal end of the syringe body and the stopper. Examples of a therapeutic product include, but are not limited to, a pharmaceutical composition or a biological composition.

In some embodiments, the syringe 100 further comprises a cap 50 disposed at the distal end of the syringe body and configured to seal the first opening at the distal end for dispensing. The distal end of the syringe is configured to be attached with a needle (not shown) for injection.

In some embodiments, the stopper insert 30 is optional and the plunger rod 40 is sized and configured to be coupled with the stopper 20 directly through some configurations described for the stopper insert 30. The stopper 20 has the structural features described in the stopper insert 30 for its connection with the plunger rod 40. The first end of the plunger rod is sized and configured to be coupled directly with the stopper.

In another aspect, the present disclosure provides a kit comprising the syringe as described herein.

In another aspect, the present disclosure provides a kit comprising the syringe body, the stopper, the stopper insert, and the plunger rod as descried herein. In some embodiments, the kit includes a therapeutic product as described herein. These components can be assembled to provide a syringe such as a prefilled syringe as described herein.

In another aspect, the present disclosure provides a method of making the syringe. FIG. 20 is a flowchart diagram illustrating an exemplary method 200 of making the syringe 100 in accordance with some embodiments. Such a method 200 comprises at least steps as described herein. The steps are not in a particular order as shown in FIG. 20.

At step 202, the syringe body 10, the stopper 20, the stopper insert 30, and the plunger rod 40 are provided.

At step 204, the stopper insert 30 is coupled and attached with the stopper 20 as described herein.

At step 206, the stopper insert 30 and the stopper 20 are inserted into the barrel of the syringe body 10 from the second opening of the syringe body 10.

At step 208, the plunger rod 40 is attached to the exterior of the syringe body 10 as described herein.

In some embodiments, the method 200 further comprises a step 210 of filling a pre-determined amount of a therapeutic product into a portion of the interior volume between the first opening and the stopper 20.

In another aspect, the present disclosure provides a method of using the syringe and the kit as described herein. FIG. 21 is a flowchart diagram illustrating an exemplary method 300 of using the exemplary syringe 100 in accordance with some embodiments. The method 300 comprises steps as described herein.

For example, at step 304, the plunger rod 40 is detached from the syringe body 10. At step 306, the plunger rod 40 is assembled with the stopper insert 30 (or the stopper 20) inside the barrel. The first end of the plunger rod 10 is coupled with a proximal end of the stopper insert 30.

Although the subject matter has been described in terms of exemplary embodiments, it is not limited thereto. Rather, the appended claims should be construed broadly, to include other variants and embodiments, which may be made by those skilled in the art.

What is claimed is:

1. A syringe comprising:

a syringe body having a distal end, a proximal end, and a barrel between the distal end and the proximal end and having a barrel wall defining an interior volume, the syringe body further defining a first opening at the distal end for dispensing and a second opening at the proximal end;

a stopper disposed inside the barrel and configured to seal the interior volume; and a plunger rod disposed outside the syringe body, the plunger rod having a first end, a second end, and a middle section, the middle section disposed along the barrel wall, wherein the second end of the plunger rod is reversibly attached to the distal end of the syringe body, the second end of the plunger rod comprises a plunger flange having a cutout and is configured to circumferentially encircle at least partially but less fully and engage the distal end of the syringe body in a retaining manner through the cutout of the plunger flange, the syringe body comprises a barrel flange on the proximal end, the plunger rod defines a concave portion in the first end, wherein the concave portion is a notch normal to the middle section of the plunger rod, and is configured to accept and retain a portion of the barrel flange of the syringe body and encompass a portion of the second opening, and a surface of the notch extends along the barrel flange and partially covers the second opening, and the plunger rod is configured to be fully removable from the syringe body during use and assembled by a user so as to drive the stopper in a direction from the proximal end to the distal end of the syringe body.

2. The syringe of claim 1, wherein the plunger rod comprises a snap cylinder, and the concave portion is between the snap cylinder and the middle section.

3. The syringe of claim 1, wherein the plunger rod is configured to be detached and assembled with the stopper.

4. The syringe of claim 1, further comprising a stopper insert having a distal portion and a proximal portion, the stopper insert disposed inside the barrel and coupled with the stopper at the distal portion, wherein the plunger rod is configured to be detached and assembled with the stopper insert.

5. The syringe of claim 4, wherein the first end of the plunger rod comprises a raised lip configured to form a mechanical interlock with a cantilever arm in the stopper insert through a snap mechanism, wherein the first end of the plunger rod is sized and configured to be coupled with the stopper insert.

6. The syringe of claim 4, wherein the proximal portion of the stopper insert is flexible and comprises threads therein, and the first end of the plunger rod comprises a barb structure having angular edged structures, wherein the barb structure is configured to be inserted into and lock with the proximal portion of the stopper insert through the angular edged structures inside the threads.

7. The syringe of claim 4, wherein the proximal portion of the stopper insert comprises a protrusion in a middle and defines a trench around the protrusion, the first end of the plunger rod defines a hole, the first end of the plunger rod is configured to be disposed in the trench, and the protrusion is configured to be disposed inside the hole to provide a male/female interlocking structure.

8. The syringe of claim 1, wherein the first end of the plunger rod comprises a patterned tip structure, the proximal portion of the stopper insert defines a patterned depression having a shape complimentary to the patterned tip structure, and the first end of the plunger rod is configured to be twistedly fitted into the proximal portion of the stopper insert.

9. The syringe of claim 1, wherein the middle section of the plunger rod has a wall with a curved surface matching with a portion of an exterior surface of the barrel wall.

10. The syringe of claim 9, wherein the middle section of the plunger rod is proximal to or in contact with the portion of the exterior surface of the barrel wall.

11. The syringe of claim 1, wherein the syringe is a prefilled syringe comprising a therapeutic product disposed inside a portion of the interior volume between the distal end of the syringe body and the stopper.

12. The syringe of claim 1, further comprising a cap disposed at the distal end of the syringe body and configured to seal the first opening at the distal end for dispensing.

13. The syringe of claim 1, wherein the distal end of the syringe is configured to be attached with a needle.

14. A kit comprising the syringe of claim 1.

15. A method of making the syringe of claim 1, comprising:

providing the syringe body, the stopper, and the plunger rod; and attaching the plunger rod to the syringe body.

16. The method of claim 15, further comprising providing a stopper insert;

coupling the stopper insert and the stopper; and inserting the stopper insert and the stopper into the barrel of the syringe body from the second opening.

17. The method of claim 15, further comprising:

filling a pre-determined amount of a therapeutic product into a portion of the interior volume between the distal end of the syringe body and the stopper.

18. A method of using the syringe of claim 1, comprising:

detaching the plunger rod from the syringe body; and assembling the plunger rod with the stopper or a stopper insert inside the barrel, wherein the first end of the plunger rod is coupled with a proximal end of the stopper or the stopper insert.

* * * * *